United States Patent
Fujikura

(10) Patent No.: US 12,283,068 B2
(45) Date of Patent: Apr. 22, 2025

(54) MEDICAL IMAGE PROCESSING DEVICE, ENDOSCOPE SYSTEM, AND MEDICAL IMAGE PROCESSING DEVICE OPERATION METHOD

(71) Applicant: FUJIFILM Corporation, Tokyo (JP)

(72) Inventor: Tetsuya Fujikura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 471 days.

(21) Appl. No.: 17/749,792

(22) Filed: May 20, 2022

(65) Prior Publication Data

US 2022/0375117 A1 Nov. 24, 2022

(30) Foreign Application Priority Data

May 24, 2021 (JP) ................................. 2021-087028

(51) Int. Cl.
*G06T 7/70* (2017.01)
*A61B 1/00* (2006.01)
(Continued)

(52) U.S. Cl.
CPC .......... *G06T 7/70* (2017.01); *A61B 1/000094* (2022.02); *A61B 5/489* (2013.01);
(Continued)

(58) Field of Classification Search
CPC ..................... G06T 7/70; G06T 7/0012; G06T 2207/10068; G06T 2207/20081;
(Continued)

(56) References Cited

U.S. PATENT DOCUMENTS 7,965,878 B2 * 6/2011 Higuchi ............... A61B 1/0002
382/128
2013/0265401 A1 10/2013 Igarashi et al.
(Continued)

FOREIGN PATENT DOCUMENTS

JP 2014-226341 A 12/2014
JP 2021-029979 A 3/2021
(Continued)

OTHER PUBLICATIONS

Sadda et al.; "Deep-learned placental vessel segmentation for intraoperative video enhancement in fetoscopic surgery"; International Journal of Computer Assisted Radiology and Surgery; Springer, Nov. 27, 2018; pp. 227-235; vol. 14, No. 2; XP037012486.
(Continued)

*Primary Examiner* — Md K Talukder
(74) *Attorney, Agent, or Firm* — Studebaker Brackett PLLC

(57) ABSTRACT

A medical image processing device acquires a medical image, detects a position of a specific blood vessel having a predetermined thickness or more on the basis of the medical image, and performs control for outputting specific blood vessel position information regarding the position of the specific blood vessel to provide a notification. The detection of the position of a specific blood vessel is performed by using a learning image that is the medical image associated with information regarding a position of at least a part of the specific blood vessel.

14 Claims, 18 Drawing Sheets

(51) Int. Cl.
*A61B 5/00* (2006.01)
*G06T 7/00* (2017.01)

(52) U.S. Cl.
CPC .. *G06T 7/0012* (2013.01); *G06T 2207/10068* (2013.01); *G06T 2207/20081* (2013.01); *G06T 2207/30101* (2013.01)

(58) Field of Classification Search
CPC ............. G06T 2207/30101; G06T 7/11; G06T 2207/10152; G06T 7/74; G06T 2207/20084; G06T 7/73; A61B 1/000094; A61B 5/489; A61B 1/0005; A61B 1/00055; A61B 1/0638; A61B 1/0655; A61B 2017/00269; A61B 1/000096; A61B 1/00009; A61B 1/04; A61B 1/0646; A61B 1/0684
See application file for complete search history.

(56) References Cited

U.S. PATENT DOCUMENTS

| | | | |
|---|---|---|---|
| 2013/0293693 A1 | 11/2013 | Igarashi et al. | |
| 2015/0003715 A1* | 1/2015 | Tomoto | G06V 10/44 382/133 |
| 2016/0038004 A1 | 2/2016 | Tanaka | |
| 2018/0214004 A1* | 8/2018 | Kamon | A61B 5/14552 |
| 2018/0276823 A1* | 9/2018 | Barral | A61B 5/7425 |
| 2019/0038111 A1* | 2/2019 | Endo | A61B 1/000094 |
| 2020/0211190 A1* | 7/2020 | Jørgensen | A61B 1/044 |
| 2020/0297422 A1* | 9/2020 | Gocho | A61B 1/00055 |
| 2020/0372638 A1* | 11/2020 | Gregson | G16H 50/70 |
| 2021/0000436 A1* | 1/2021 | Zhao | A61B 6/582 |
| 2021/0345867 A1* | 11/2021 | Georgakoudi | G02B 23/2469 |
| 2023/0360298 A1* | 11/2023 | Kubota | G06T 7/11 |

FOREIGN PATENT DOCUMENTS

| | | |
|---|---|---|
| WO | 2013/145409 A1 | 10/2013 |
| WO | 2013/145410 A1 | 10/2013 |
| WO | 2020/023740 A1 | 1/2020 |

OTHER PUBLICATIONS

Casella et al.; "NephCNN: A deep-learning framework for vessel segmentation in nephrectomy laparoscopic videos"; 2020 25th International Conference on Pattern Recognition (ICPR); IEEE; Jan. 10, 2021; pp. 6144-6149; XP033908721.

The extended European search report issued by the European Patent Office on Oct. 18, 2022, which corresponds to European Patent Application No. 22175197.7-1126 and is related to U.S. Appl. No. 17/749,792.

"Notice of Reasons for Refusal" Office Action issued in JP 2021-087028; mailed by the Japanese Patent Office on Oct. 8, 2024.

"Decision of Refusal" Office Action issued in JP 2021-087028; mailed by the Japanese Patent Office on Mar. 4, 2025.

* cited by examiner

MEDICAL IMAGE PROCESSING DEVICE, ENDOSCOPE SYSTEM, AND MEDICAL IMAGE PROCESSING DEVICE OPERATION METHOD

CROSS-REFERENCE TO RELATED APPLICATIONS

This application claims priority under 35 U.S.C § 119(a) to Japanese Patent Application No. 2021-087028 filed on 24 May 2021. The above application is hereby expressly incorporated by reference, in its entirety, into the present application.

BACKGROUND OF THE INVENTION

1. Field of the Invention

The present invention relates to a medical image processing device, an endoscope system, and a medical image processing device operation method.

2. Description of the Related Art

Endoscopic submucosal dissection (ESD) makes it possible to resect tumors or the like with a size to which endoscopic mucosal resection (EMR) cannot be applied and thus to complete an operation without selecting a highly invasive surgery. ESD is performed endoscopically, and thus has the advantage of being minimally invasive. On the other hand, a doctor who is an operator is required to perform ESD with limited information based on an image (hereinafter referred to as an endoscopic image) obtained by imaging an observation target of an endoscope, which is a subject, with the endoscope. Thus, unintended damage to blood vessels, or muscular layers may occur.

There is an endoscopic device that displays an image obtained by emphasizing a first image signal on the basis of a difference between the first image signal and a second image signal each of which has a peak wavelength of a specific spectral characteristic, so that blood vessels in the deep mucous membrane can be clearly displayed. According to this endoscopic device, blood vessels in the deep mucous membrane can be clearly displayed without performing complicated work such as drug administration (WO2013/145409A1, corresponding to US2013/293693A1).

SUMMARY OF THE INVENTION

For example, ESD for resecting a tumor is performed according to procedures such as marking around the tumor, local injection into the submucosal layer, incision of the mucous membrane, peeling of the submucosal layer, and hemostasis. In a case where the submucosal layer is incised and peeled off, it is desirable that no unintended damage to blood vessels or the like occurs.

In a case where a blood vessel itself is visible, the blood vessel in the deep mucous membrane is emphasized and clearly displayed, and thus it is possible to coagulate the blood vessel in advance or to perform incision by avoid the blood vessel. However, in ESD, the visibility of the blood vessel itself may decrease. For example, because ESD is performed on the basis of an endoscopic image, fibrosis may be present in a part or the whole of the submucosal layer in the endoscopic image, blood vessels in the fibrosis may be hardly visually recognized. The visibility becomes poor due to dirt on an image pick-up lens portion of the endoscope, generation of mist, or the like.

The present invention provides a medical image processing device, an endoscope system, and a medical image processing device operation method capable of detecting and outputting even a blood vessel having reduced visibility in an endoscopic image.

According to an aspect of the present invention, there is provided a medical image processing device including a processor, in which the processor acquires a medical image obtained by imaging a subject with an endoscope, detects a position of a specific blood vessel that is a blood vessel included in the subject captured in the medical image and has a predetermined thickness or more on the basis of the medical image, and performs control for outputting specific blood vessel position information regarding the position of the specific blood vessel to provide a notification, and the detection of the position of the specific blood vessel is performed by using a learning image that is the medical image associated with information regarding a position of at least a part of the specific blood vessel included in the subject captured in the medical image.

The learning image is preferably the medical image in which the subject includes a submucosal layer.

The learning image is preferably the medical image in which the subject includes fibrosis.

The learning image is preferably the medical image in which the subject includes a cautery scar, coagulated blood, and/or fat.

The learning image is preferably the medical image associated with information indicating that there is no specific blood vessel.

The learning image is preferably the medical image associated with information obtained by a doctor visually observing the medical image.

The learning image is preferably the medical image associated with information obtained by performing image processing on the medical image.

The learning image is preferably the medical image associated with information obtained by performing image processing on the medical image obtained by imaging the subject illuminated by illumination light having a predetermined spectrum.

Preferably, the processor includes a learning model that has performed learning by using the learning image, and the detection of the specific blood vessel is performed by using the learning model.

The specific blood vessel position information preferably includes information regarding an incision suitable site where safe incision is possible.

The processor preferably performs control for outputting the specific blood vessel position information with at least one of a color, a figure, a symbol, and a character.

The processor preferably performs control for outputting the specific blood vessel position information with sound and/or light.

According to another aspect of the present invention, there is provided an endoscope system including the medical image processing device; a light source that emits illumination light that illuminates a subject; and an endoscope that images the subject.

According to still another aspect of the present invention, there is provided a medical image processing device operation method of performing control for acquiring a medical image obtained by imaging a subject with an endoscope; detecting a position of a specific blood vessel that is a blood vessel included in the subject captured in the medical image and has a predetermined thickness or more on the basis of the medical image; and outputting specific blood vessel position information regarding the position of the specific blood vessel to provide a notification, in which the detection of the position of the specific blood vessel is performed by using a learning image that is the medical image associated with information regarding a position of at least a part of the specific blood vessel included in the subject captured in the medical image.

According to the present invention, even a blood vessel having reduced visibility in an endoscopic image can be detected and output.

DESCRIPTION OF THE PREFERRED EMBODIMENTS

Figure 1:
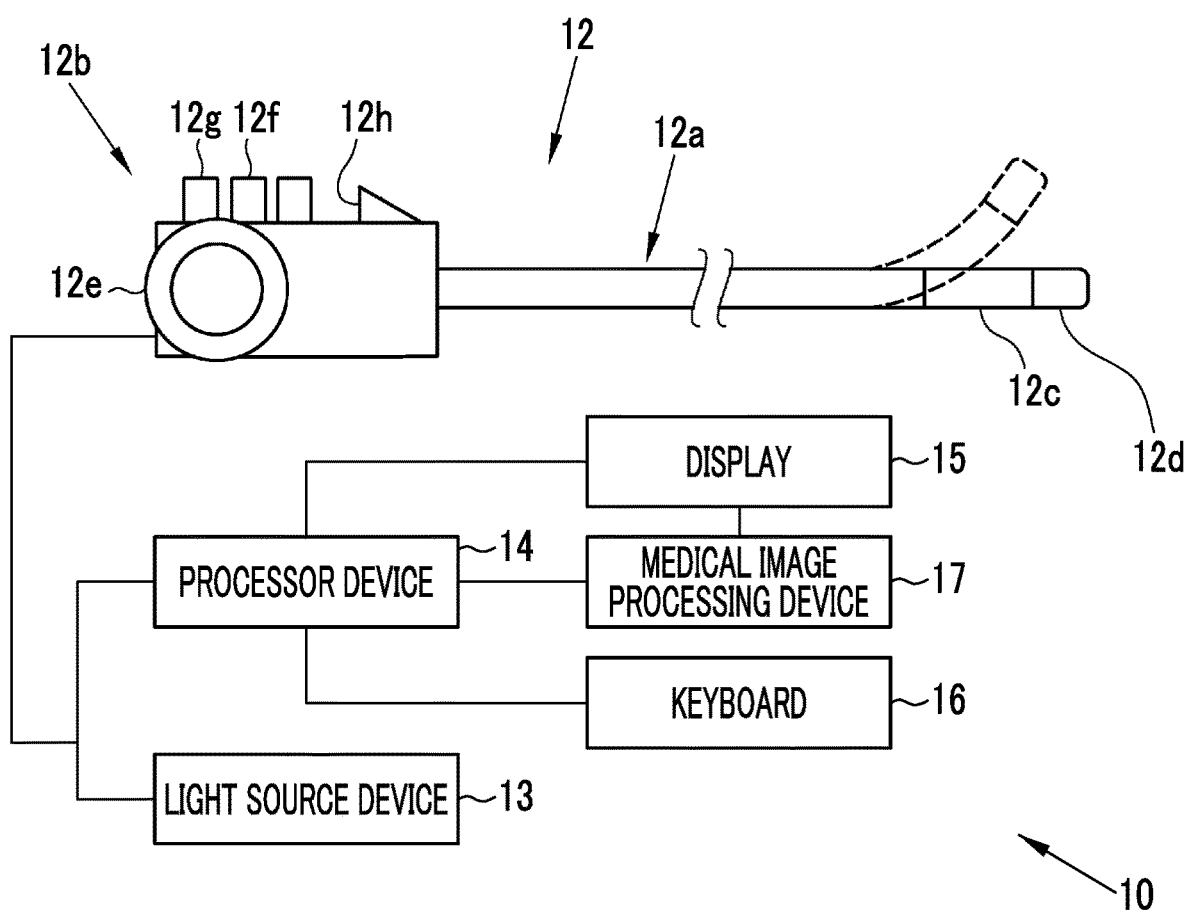
FIG. 1 is an external view of an endoscope system.

As shown in FIG. 1, an endoscope system 10 includes an endoscope 12, a light source device 13, a processor device 14, a display 15, a keyboard 16, and a medical image processing device 17. The endoscope 12 is optically connected to the light source device 13 and electrically connected to the processor device 14. The processor device 14 is connected to the medical image processing device 17. The medical image processing device 17 acquires an endoscopic image that is a medical image from the processor device 14, and performs various processes for acquiring various types of information and the like.

In the present embodiment, the medical image is an endoscopic image. In the present embodiment, the medical image processing device 17 and the processor device 14 are separate devices, but a device that functions as the medical image processing device 17 may be disposed in the processor device 14, and the processor device 14 may perform the function of the processing device 17. The various connections are not limited to wired connections, and may be wireless connections, or may be connections using a network. Therefore, the function of the medical image processing device 17 may be performed by an external device connected thereto via a network.

The endoscope 12 is provided on an insertion part 12a to be inserted into the body of a subject having an observation target, an operating part 12b provided at a base end portion of the insertion part 12a, and a bendable part 12c and a tip part 12d provided at a distal end side of the insertion part 12a. The bendable part 12c is curved by operating an angle knob 12e (refer to FIG. 2) of the operating part 12b. The tip part 12d is directed in a desired direction when the bending portion 12c is curved. A forceps channel (not shown) for inserting a treatment tool or the like is provided from the insertion part 12a to the tip part 12d. The treatment tool is inserted into the forceps channel from the forceps port 12h.

The operating part 12b includes a zoom operating part 12f for changing an image pick-up magnification and a mode selector switch 12g used for an observation mode switching operation, in addition to the angle knob 12e. An observation mode switching operation or a zoom operation may be an operation or an instruction using a keyboard 16 or a foot switch (not shown) in addition to the mode selector switch 12g or the zoom operating part 12f.

The endoscope system 10 has three observation modes such as a normal observation mode, a special observation mode, and a multi-observation mode. The normal observation mode is a mode in which a normal image, which is an image of a natural color obtained by picking up an image of an observation target by using white light as illumination light, is displayed on the display 15. The special observation mode is a mode for displaying a special image different from that using white light on the display 15. The special image may be obtained, for example, by emitting illumination light having a specific spectrum to acquire a special image of an observation target, or performing specific image processing. As the special image, an endoscopic image emphasizing a specific structure or the like is preferably displayed on the display 15. The emphasis on a specific structure includes emphasis on blood vessels or gland ducts, and the emphasis on blood vessels includes emphasis on superficial blood vessels, middle-layer blood vessels, or deep blood vessels. The emphasis on blood vessels will be described later.

The multi-observation mode is a mode in which the normal observation mode and the special observation mode are automatically switched, and a normal image and a special image can be acquired. The display 15 may be set as appropriate such that only a normal image is displayed, or a normal image is displayed as a main image and a special image is displayed as a sub-image.

The processor device 14 is electrically connected to the display 15 and the keyboard 16. The display 15 displays, for example, a normal image, a special image, and/or various types of information. The keyboard 16 functions as a user interface that receives input operations such as function settings. An external storage (not shown) for storing images, image information, and the like may be connected to the processor device 14.

Figure 2:
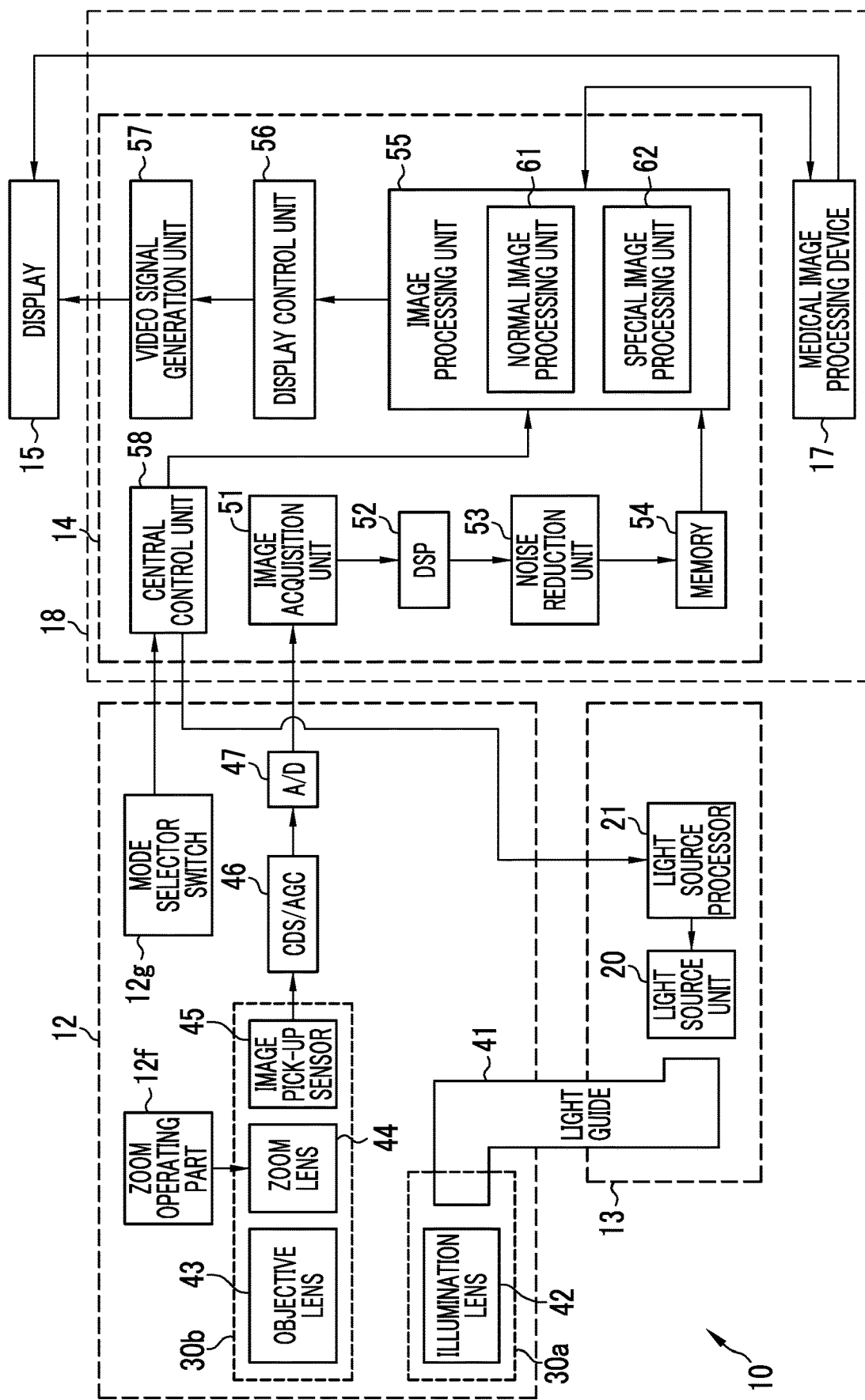
FIG. 2 is a block diagram showing a function of the endoscope system.

As shown in FIG. 2, the light source device 13 includes a light source unit 20 that emits illumination light to irradiate an observation target, and a light source processor 21 that controls the light source unit 20. The light source unit 20 is configured with, for example, a semiconductor light source such as multi-color light emitting diodes (LEDs), a combination of a laser diode and a phosphor, or a xenon lamp or a halogen light source. The light source unit 20 includes an optical filter or the like for adjusting a wavelength band of light emitted by the LED or the like. The light source processor 21 controls an amount of illumination light by turning on/off each LED and the like and adjusting a drive current or a drive voltage of each LED and the like. The light source processor 21 controls a wavelength band of the illumination light by changing an optical filter or the like.

Figure 3:
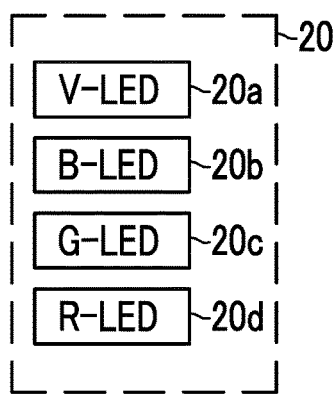
FIG. 3 is an explanatory diagram for describing four-color LEDs included in a light source unit.

As shown in FIG. 3, in the present embodiment, the light source unit 20 includes four color LEDs such as a violet light emitting diode (V-LED) 20a, a blue light emitting diode (B-LED) 20b, and a green light emitting diode (G-LED) 20c, and a red light emitting diode (R-LED) 20d.

Figure 4:
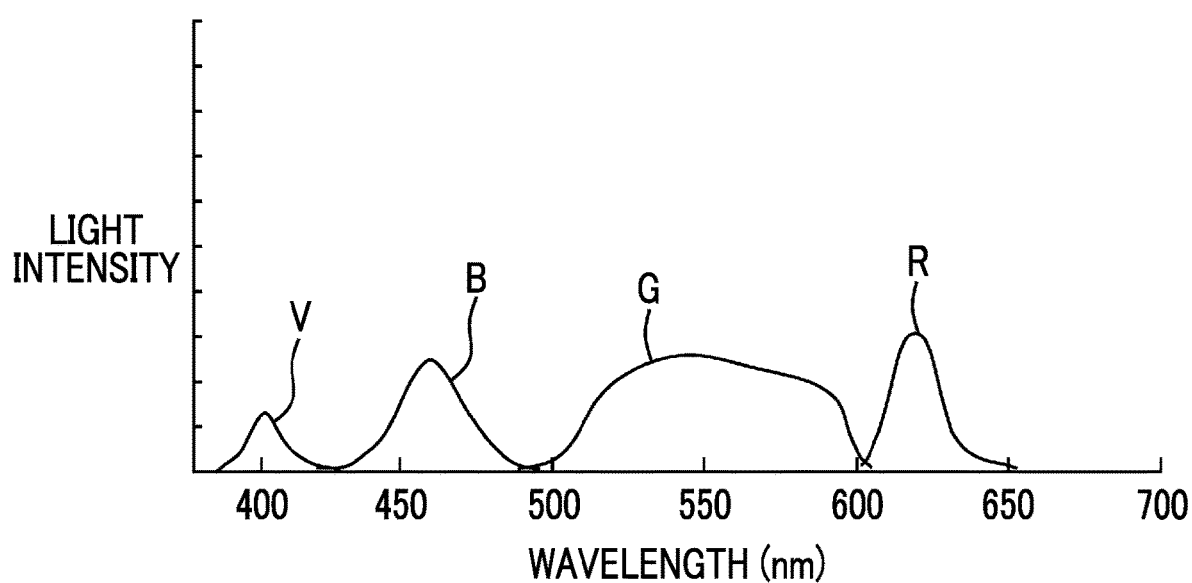
FIG. 4 is a graph showing spectra of violet light V, blue light B, green light G, and red light R.

As shown in FIG. 4, the V-LED 20a generates violet light V having a central wavelength of 410±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm.

The light source processor 21 controls the V-LED 20a, the B-LED 20b, the G-LED 20c, and the R-LED 20d. In the normal observation mode, the light source processor 21 controls the respective LEDs 20a to 20d such that normal light in which a combination of the light intensity ratios of the violet light V, the blue light B, the green light G, and the red light R is Vc:Bc:Gc:Rc is emitted.

Figure 5:
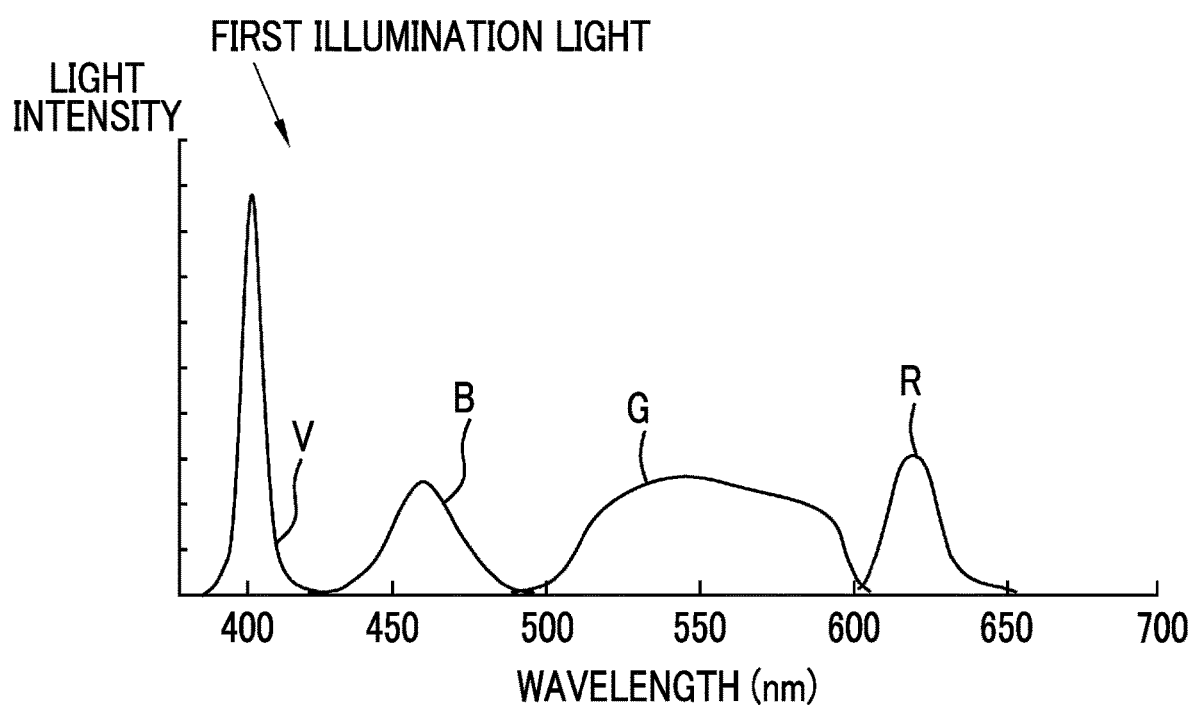
FIG. 5 is a graph showing a spectrum of first illumination light.

In a case where the special observation mode is set, for example, the processor 21 controls the respective LEDs 20a to 20d such that first illumination light in which a combination of the light intensity ratios between the violet light V, the blue light B, the green light G, and the red light R is Vs1:Bs1:Gs1:Rs1 is emitted. In a case where superficial blood vessels are emphasized with the first illumination light, it is preferable that the light intensity of the violet light V is higher than the light intensity of the blue light B. For example, as shown in FIG. 5, a ratio between the light intensity Vs1 of the violet light V and the light intensity Bs1 of the blue light B is set to "4:1".

In the present specification, a combination of light intensity ratios includes a case where a ratio of at least one semiconductor light source is 0 (zero). Therefore, this includes a case where any one or more of the semiconductor light sources are not turned on. For example, as in a case where a combination of the light intensity ratios between the violet light V, the blue light B, the green light G, and the red light R is 1:0:0:0, even in a case where only one of the semiconductor light sources is turned on, and the other three are not turned on, a light intensity ratio is applied and is one of combinations of light intensity ratios.

As described above, combinations of the light intensity ratios of the violet light V, the blue light B, the green light G, and the red light R emitted in the normal observation mode or the special observation mode, that is, the types or spectra of the illumination light are different from each other. In the multi-observation mode, illumination light of different types or spectra is automatically switched and emitted. An observation mode using illumination light of a different type or spectrum having different a combination of light intensity ratios different from that of illumination light used in these observation modes may be used.

In a case where the multi-observation mode is set, the light source processor 21 may switch and emit a specific type of illumination light. Specifically, a normal light period in which the normal light is continuously emitted and the first illumination light period in which the first illumination light is continuously emitted are alternately repeated. Specifically, after the normal light period in which the normal light is emitted is performed in a predetermined number of frames, the first illumination light period in which the first illumination light is emitted is performed in a predetermined number of frames. After that, the normal light period is set again, and the set of the normal light period and the first illumination light period is repeated.

The "frame" means a unit for controlling an image pick-up sensor 45 (refer to FIG. 2) that picks up an image of an observation target. For example, "1 frame" means a period including at least an exposure period in which the image pick-up sensor 45 is exposed with light from the observation target and a reading period in which an image signal is read. In the present embodiment, various periods such as the normal light period or the first illumination light period are defined to correspond to a "frame" which is the unit of imaging.

Figure 6:
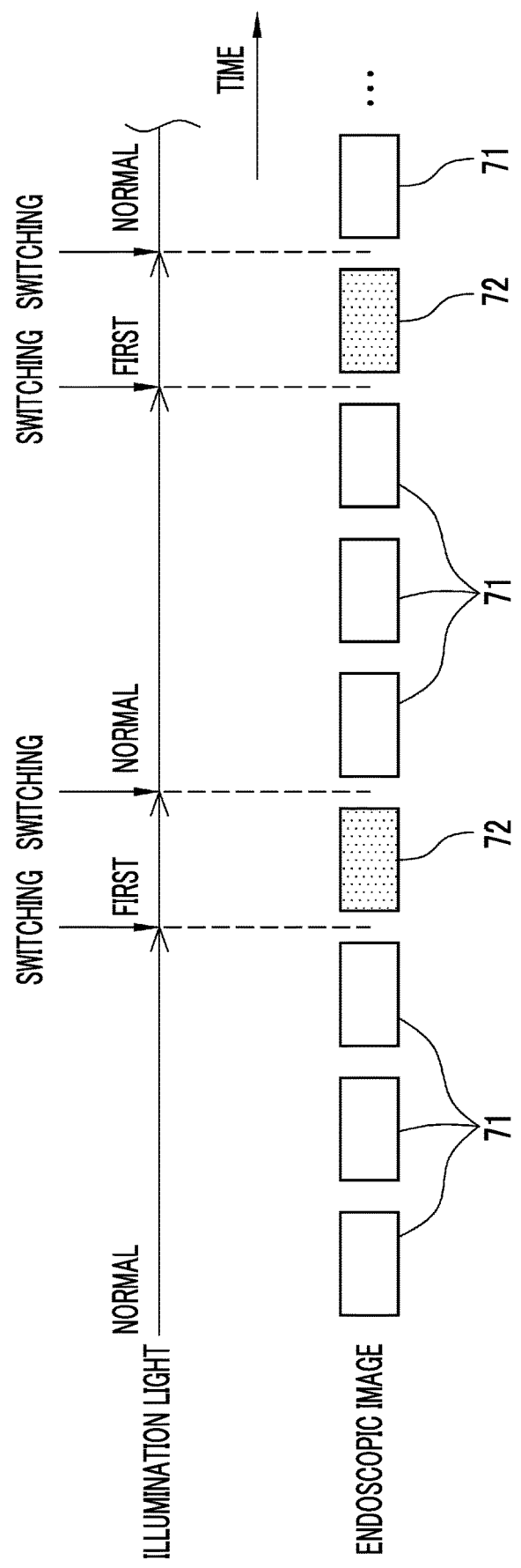
FIG. 6 is an explanatory diagram for describing the types and order of endoscopic images picked up by the endoscope system.

As shown in FIG. 6, in the multi-observation mode, for example, the illumination light is switched after the normal light period for emitting the normal light written as "normal" in an illumination light column is performed for a period of 3 frames, and the first illumination light period for emitting the first illumination light written as "first" in the illumination light column is performed for a period of one frame. After that, the normal light period is set again, and the set of the normal light period and the first illumination light period is repeated for 4 frames. Therefore, three normal images 71 are continuously captured during three frames of the normal light period, and then one first image 72 is captured during the first illumination light period. In the figure, the first image 72 is shaded because a color tone is different from that of the normal image 71. After that, the normal light period is returned, and this pattern is continuously repeated.

The light emitted by each of the LEDs 20a to 20e is incident to a light guide 41 via an optical path coupling portion (not shown) configured with a mirror, a lens, and the like. The light guide 41 is built in the endoscope 12 and a universal cord (a cord connecting the endoscope 12, the light source device 13, and the processor device 14 to each other). The light guide 41 propagates light from the optical path coupling portion to the tip part 12d of the endoscope 12.

An illumination optical system 30a and an image pick-up optical system 30b are provided at the tip part 12d of the endoscope 12. The illumination optical system 30a has an illumination lens 42, and the illumination light propagated by the light guide 41 is applied to the observation target via the illumination lens 42. The image pick-up optical system 30b has an objective lens 43, a zoom lens 44, and an image pick-up sensor 45. Various types of light such as reflected light, scattered light, and fluorescence from the observation target are incident to the image pick-up sensor 45 via the objective lens 43 and the zoom lens 44. Consequently, an image of the observation target is formed on the image pick-up sensor 45. The zoom lens 44 freely moves between the telephoto end and the wide-angle end by operating the zoom operating part 12f, and enlarges or reduces the image of the observation target formed on the image pick-up sensor 45.

The image pick-up sensor 45 is a color image pick-up sensor provided with one of a red (R), green (G), or blue (B) color filter for each pixel, and picks up an image of the observation target to output an image signal of each color of RGB. As the image pick-up sensor 45, a charge coupled device (CCD) image pick-up sensor or a complementary metal oxide semiconductor (CMOS) image pick-up sensor may be used. Instead of the image pick-up sensor 45 provided with the primary color filter, a complementary image pick-up sensor provided with cyan (C), magenta (M), yellow (Y), and G (green) complementary filters may be used. In a case where a complementary image pick-up sensor is used, image signals of four colors of CMYG are output. Therefore, the same RGB image signals as in the image pick-up sensor 45 can be obtained by converting image signals of the four colors of CMYG into image signals of the three colors of RGB through complementary-primary color conversion. Instead of the image pick-up sensor 45, a monochrome sensor without a color filter may be used.

The image pick-up sensor 45 is driven and controlled by an image pick-up control unit (not shown). A central control unit 58 (refer to FIG. 2) controls light emission of the light source unit 20 via the light source processor 21 in synchronization with the image pick-up control unit, and thus in the normal observation mode, an image of an observation target illuminated by the normal light is picked up. Consequently, a Bc image signal is output from a B pixel of the image pick-up sensor 45, a Gc image signal is output from a G pixel, and an Rc image signal is output from an R pixel. In the special observation mode, the central control unit 58 controls light emission of the light source unit 20 to control the image pick-up sensor 45 such that an image of an observation target illuminated by the first illumination light is picked up. Consequently, in the special observation mode, a Bs1 image signal is output from the B pixel of the image pick-up sensor 45, a Gs1 image signal is output from the G pixel, and an Rs1 image signal is output from the R pixel.

In the multi-observation mode, the central control unit 58 (refer to FIG. 2) controls light emission of the light source unit 20 to control the image pick-up sensor 45 such that an image of an observation target illuminated by the normal light and the first illumination light is picked up for respective preset periods. Consequently, in the multi-observation mode, a Bc image signal is output from the B pixel of the image pick-up sensor 45, a Gc image signal is output from the G pixel, and an Rc image signal is output from the R pixel during the normal light period. During the first illumination light period, the Bs1 image signal is output from the B pixel of the image pick-up sensor 45, the Gs1 image signal is output from the G pixel, and the Rs1 image signal is output from the R pixel.

A correlated double sampling/automatic gain control (CDS/AGC) circuit 46 performs correlated double sampling (CDS) or automatic gain control (AGC) on an analog image signal obtained from the image pick-up sensor 45. The image signal that has passed through the CDS/AGC circuit 46 is converted into a digital image signal by an analog/digital (A/D) converter 47. The digital image signal after A/D conversion is input to the processor device 14.

In the processor device 14, a program related to processes such as image processing is stored in a program memory (not shown). In the processor device 14, the program in the program memory is operated by the central control unit 58 configured with an image processor or the like that is a first processor, to realize functions of an image acquisition unit 51, a digital signal processor (DSP) 52, a noise reduction unit 53, a memory 54, an image processing unit 55, a display control unit 56, a video signal generation unit 57, and the central control unit 58. The central control unit 58 receives information from the endoscope 12 and the light source device 13, and controls each unit of the processor device 14 and also controls the endoscope 12 or the light source device 13 on the basis of the received information. The central control unit 58 also receives information such as instructions from the keyboard 16.

The image acquisition unit 51 acquires a digital image signal for an endoscopic image input from the endoscope 12. The image acquisition unit 51 acquires an image signal obtained by imaging an observation target illuminated by each type of illumination light for each frame. The image acquisition unit 51 may acquire an endoscopic image obtained by imaging an observation target illuminated by types of illumination light having predetermined and different spectra.

The acquired image signal is transmitted to the DSP 52. The DSP 52 performs digital signal processing such as a color correction process on the received image signal. The noise reduction unit 53 performs a noise reduction process based on, for example, a moving average method, or a median filter method on the image signal subjected to the color correction process or the like by the DSP 52. The image signal with reduced noise is stored in the memory 54.

The image processing unit 55 acquires an image signal after noise reduction from the memory 54. The acquired image signal is subjected to signal processing such as a color conversion process, a color enhancement process, and a structure enhancement process as necessary to generate a color endoscopic image in which the observation target is captured. The image processing unit 55 includes a normal image processing unit 61 and a special image processing unit 62.

In the image processing unit 55, the normal image processing unit 61 performs image processing for the normal image such as a color conversion process, a color enhancement process, and a structure enhancement process on the input image signal for the normal image after noise reduction for one frame in the normal observation mode or the multi-observation mode. The image signal subjected to the image processing for a normal image is input to the medical image processing device 17 and/or the display control unit 56.

In the special observation mode or the multi-observation mode, the special image processing unit 62 performs image processing for the first image such as a color conversion process, a color enhancement process, and a structure enhancement process on the input image signal for the first image after noise reduction for one frame. The image signal subjected to image processing for the first image is input to the medical image processing device 17 and/or the display control unit 56 as the first image 72. The image processing unit 55 may adjust a frame rate in a case where the endoscopic image is input to the medical image processing device 17 and/or the display control unit 56.

The endoscopic image generated by the image processing unit 55 is the normal image 71 in a case where an observation mode is the normal observation mode, and is the first image 72 in a case where an observation mode is the special observation mode, and details of the color conversion process, the color enhancement process, and the structure enhancement process differ depending on the observation modes. In the normal observation mode, the image processing unit 55 generates the normal image 71 by performing the various types of signal processing described above such that the observation target has a natural hue. In the special observation mode, the image processing unit 55 generates the first image 72 by, for example, performing the various types of signal processing for emphasizing a blood vessel of the observation target.

The semiconductor light sources include the V-LED 20a that emits violet light V (first narrow band light) having the central wavelength of 410±10 nm and the wavelength range of 420 to 500 nm, and the B-LED 20b that emits blue light B (second narrow band light) having the central wavelength of 450±10 nm and the wavelength range of 380 to 420 nm. Therefore, in the first image 72 generated by the image processing unit 55, a blood vessel (so-called a superficial blood vessel) or blood located at a relatively shallow position in the observation target with the surface of the mucous membrane as a reference is magenta (for example, brown). Therefore, in the first image 72, the blood vessel or bleeding (blood) of the observation target is emphasized by the difference in color with respect to the mucous membrane represented by a pinkish color.

The display control unit 56 receives the endoscopic image generated by the image processing unit 55 and performs control for displaying the endoscopic image on the display 15. The endoscopic image controlled to be displayed by the display control unit 56 is generated as a video signal to be displayed on the display 15 by the video signal generation unit 57, and is sent to the display 15. The display 15 displays the endoscopic image sent from the video signal generation unit 57 under the control of the display control unit 56.

The medical image processing device 17 acquires the endoscopic image generated by the image processing unit 55, detects a position of a specific blood vessel that is a blood vessel included in the observation target captured in the endoscopic image and has a predetermined thickness or more on the basis of the endoscopic image, and performs control for outputting specific blood vessel position information regarding the detected position of the specific blood vessel to the display 15 or the like.

The medical image processing device 17 is a general-purpose PC provided with a processor, and exhibits various functions with installation of software. In the same manner as in the processor device 14, the medical image processing device 17 also stores a program related to processes such as an image analysis process in a program memory (not shown). In the medical image processing device 17, a central control unit 81 (refer to FIG. 7) configured with an image processor or the like that is a second processor operates the program in the program memory to realize functions of a medical image acquisition unit 82, a detection unit 83, an information output unit 84, and an information display control unit 85 (refer to FIG. 7).

The medical image processing device 17 is connected to the display 15, and the display 15 displays various types of information generated and output by the medical image processing device 17. Various devices may be connected to the medical image processing device 17. Examples of various devices include a user interface such as a keyboard for giving instructions and the like, and a storage that stores data such as images and information. The medical image processing device 17 has a network connection function for connecting to various devices. The medical image processing device 17 may be connected to, for example, a medical service support device 630 (refer to FIG. 26) by the network connection function.

Figure 7:
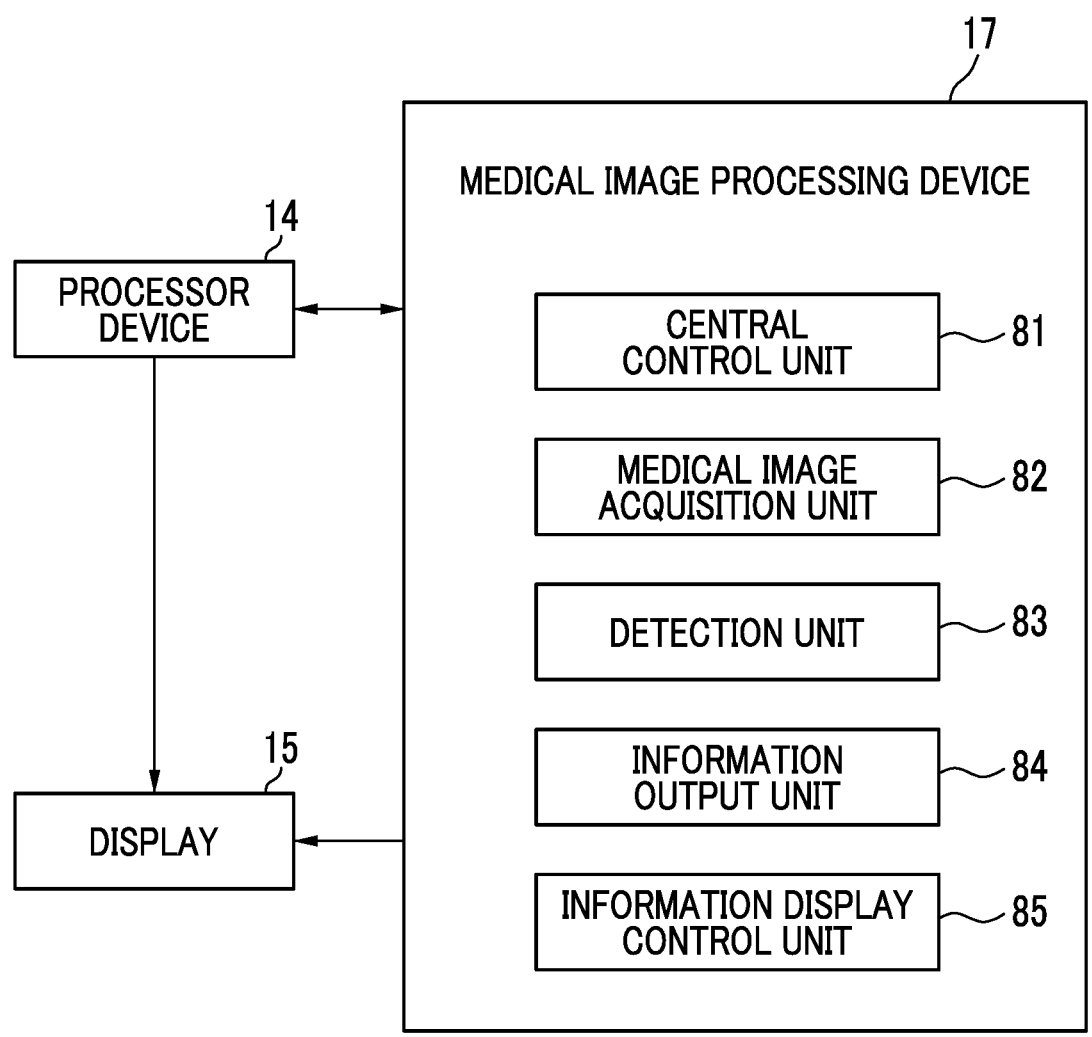
FIG. 7 is a block diagram showing a function of a medical image processing device.

As shown in FIG. 7, the medical image processing device 17 includes the central control unit 81, the medical image acquisition unit 82, the detection unit 83, the information output unit 84, and the information display control unit 85. The central control unit 81 controls each unit of the medical image processing device 17, receives information from the processor device 14 and the like, and controls each unit of the medical image processing device 17 on the basis of the received information. The central control unit 81 is also connected to a user interface such as a keyboard (not shown) and receives information such as instructions from the user interface.

The medical image acquisition unit 82 acquires a plurality of types of endoscopic images sent from the processor device 14. The acquired image is sent to the detection unit 83. The detection unit 83 detects a position of a specific blood vessel that is a blood vessel included in the observation target captured in the endoscopic image and has a predetermined thickness or more on the basis of the endoscopic image acquired by the medical image acquisition unit 82. The information output unit 84 receives information regarding the position of the specific blood vessel included in the observation target captured in the endoscopic image detected by the detection unit 83, generates specific blood vessel position information, and outputs the specific blood vessel position information such that the information is stored or a notification thereof is provided to a user such as a doctor. The information display control unit 85 receives the specific blood vessel position information from the information output unit 84 and performs control for displaying the information on the display 15.

In the present embodiment, the medical image acquisition unit 82 acquires a normal image obtained by imaging an observation target illuminated by normal light with an endoscope from the processor device 14, and sends the normal image to the detection unit 83. The detection unit 83 detects a position of a specific blood vessel that is a blood vessel included in the observation target captured in the normal image and has a predetermined thickness or more from the normal image sent from the medical image acquisition unit 82.

The specific blood vessel refers to a blood vessel having a predetermined thickness or more among blood vessels included in the observation target captured in the endoscopic image. The predetermined thickness is at least a thickness that may cause a problem in a case where damage occurs due to an ESD technique or the like. Specifically, depending on cases, in a case where the capillaries are about 10 μm, the predetermined thickness may be, for example, 0.1 mm or more. The predetermined thickness may be set depending on cases. Since there are many shapes of blood vessels, the thickness of the blood vessel refers to ab apparent width of the blood vessel and does not have to be a diameter. In the procedure of ESD, in incision of the mucous membrane and peeling of the submucosal layer, there is a probability of damaging a specific blood vessel in a case where the incision is made in the mucous membrane with a treatment tool such as a knife or a snare.

Figure 8:
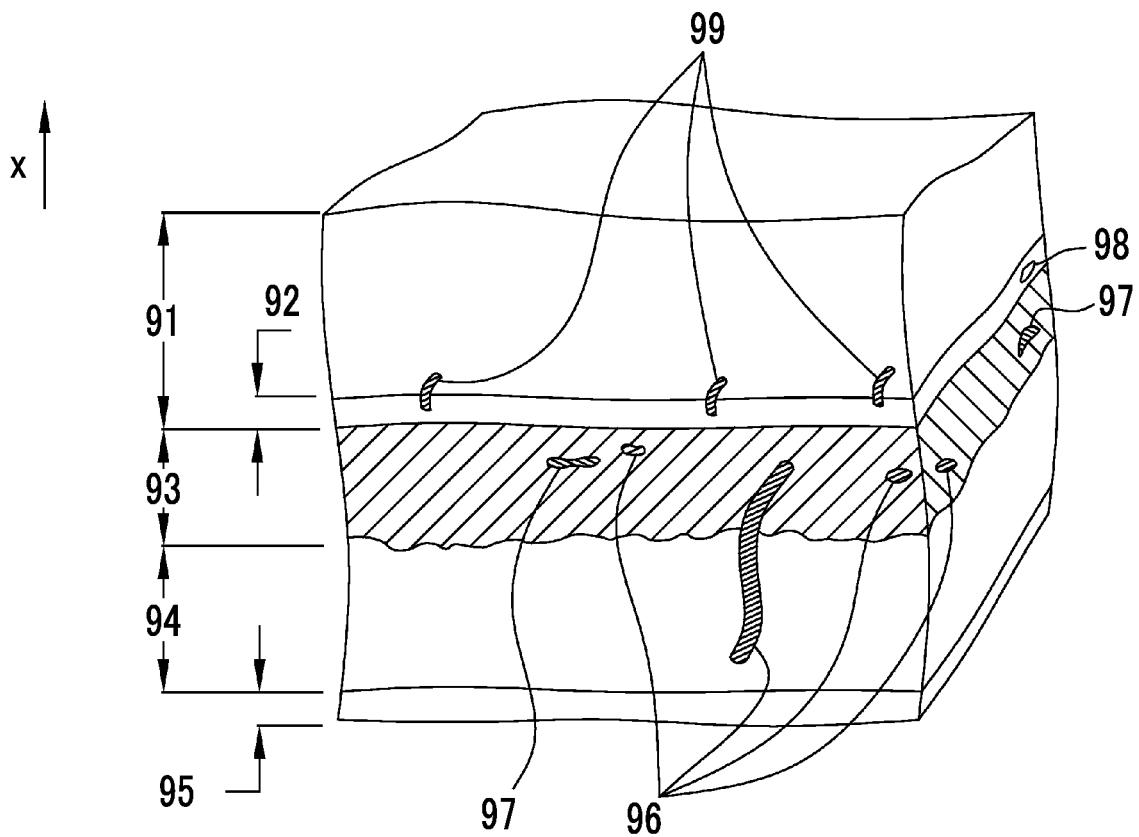
FIG. 8 is an explanatory diagram for describing a tissue of the large intestine.

As shown in FIG. 8, for example, the large intestine is constructed mainly from tissues such as the mucous membrane 91, a submucosal layer 93, a muscular layer 94, and the serosa 95. The X direction is the inside of the large intestine. The mucous membrane 91 includes a muscularis mucosae 92 between the submucosal layer 93 and the mucous membrane 91. The mucous membrane 91 includes arteries 99, lymphatic vessels 98, veins (not shown), microvessels (not shown), and the like that connect the muscularis mucosae 92 to the mucous membrane 91 inside the large intestine. The submucosal layer 93 includes penetrating blood vessels 96, veins 97, microvessels (not shown) and the like, which are relatively thick arteries connected to the muscular layer 94. The arteries 99 and microvessels are thinner than the penetrating blood vessels 96. The specific blood vessels include the penetrating blood vessels 96.

Since the penetrating blood vessel 96 included in the submucosal layer 93 is relatively thick, in a case where the penetrating blood vessel 96 is damaged during incision or peeling of the mucous membrane, an amount of bleeding is large, and once damaged, it takes time to find a damaged part due to bleeding, and it is difficult to stop bleeding. Therefore, during ESD, it is necessary to make an incision while avoiding the penetrating blood vessel 96 or the like, or to perform hemostasis treatment on the penetrating blood vessel 96 or the like in advance. As described above, it is important to ascertain a position of a specific blood vessel such as the penetrating blood vessel 96 during ESD or the like.

The position of the penetrating blood vessel 96 may be visually recognized from the endoscopic image, but it may be difficult to visually observe the presence of the penetrating blood vessel 96. For example, in a case where there is fibrosis in the submucosal layer, it may be difficult to ascertain the position of the penetrating blood vessel 96 because the fibrosis is a white opaque tissue. Due to fibrosis, only a part of the penetrating blood vessel 96 may be visible. In addition, it may be difficult to determine the position of the penetrating blood vessel 96 due to tissues such as cautery scars, coagulated blood, or fat. For example, during an ESD operation, an image pick-up lens portion of the endoscope may become dirty or mist may be generated, resulting in poor visibility and difficulty in ascertaining the position of the penetrating blood vessel 96. It may be difficult to ascertain the position of the penetrating blood vessel 96 in which bleeding occurs due to blood accumulation.

By detecting a position of a specific blood vessel such as the penetrating blood vessel 96, it is possible to prevent problems such as bleeding from occurring in a treatment such as ESD, and it is possible to avoid taking a long time for the treatment. Therefore, this contributes to the efficiency of treatment such as ESD. The position of the specific blood vessel may be a position in a two-dimensional direction in the endoscopic image or a position in a three-dimensional direction in a depth direction on the muscular layer 94 side. Therefore, by using a learning image that is an endoscopic image associated with information regarding a position of at least a part of a specific blood vessel, for example, in a case where the visibility is poor because the specific blood vessel is partly on the surface and partly inside the submucosal layer, it is possible to detect two-dimensional and three-dimensional positions of the specific blood vessel by learning in which direction the blood vessel extends.

Figure 9:
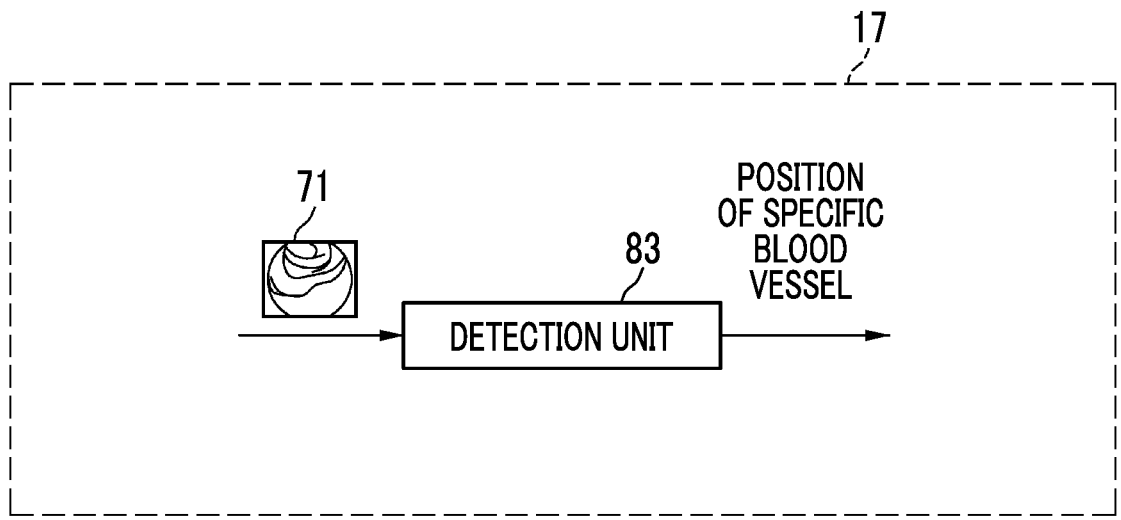
FIG. 9 is an explanatory diagram for describing a function of a detection unit.

As shown in FIG. 9, the detection unit 83 is a learning model in machine learning learned to detect a position of a specific blood vessel in an observation target captured in the normal image 71 in a case where the normal image 71 is input, and is, for example, a program. The learning model can employ various techniques in machine learning and can make various adjustments in order to detect a position of a specific blood vessel with higher accuracy. Since the position of the specific blood vessel may be obtained with higher accuracy, the detection unit 83 is preferably a multi-layer neural network model. The detection unit 83 is a learning model that detects a position of a specific blood vessel by inputting an image such as an endoscopic image, and may thus be a convolutional neural network model or a deep learning model.

The detection unit 83 is generated in advance through learning using a learning image. The learning image is an endoscopic image associated with information regarding a position of at least a part of a specific blood vessel included in an observation target captured in the endoscopic image. Specifically, since the detection unit 83 of the present embodiment detects a specific blood vessel in the ESD operation, the learning image is an endoscopic image acquired in the ESD operation, and is an endoscopic image having information regarding a position of at least a part of the specific blood vessel in an observation object captured in the endoscopic image. The association is to associate the endoscopic image with the information regarding the position of at least a part of the specific blood vessel included in the observation target captured in the endoscopic image, and it is sufficient that both are associated, and any association method may be used. So-called tagging may be performed on the endoscopic image. For example, image data of the endoscopic image may include information regarding a position of a specific blood vessel as a header or the like, or an endoscopic image and information regarding a position of a specific blood vessel stored in the form of a table may be used.

The information regarding the position of at least a part of the specific blood vessel may be obtained by a skilled doctor visually observing an endoscopic image. The information regarding the position of the specific blood vessel may be obtained through image analysis of the endoscopic image, machine learning based on the endoscopic image, or the like. For example, the position of the specific blood vessel found by the doctor can be obtained by displaying the endoscopic image on the display 15 and visually observing the image, and the position of the specific blood vessel found through image analysis or machine learning can be obtained according to a method such as recording coordinates and the like on the endoscope of the specific blood vessel.

Figure 10:
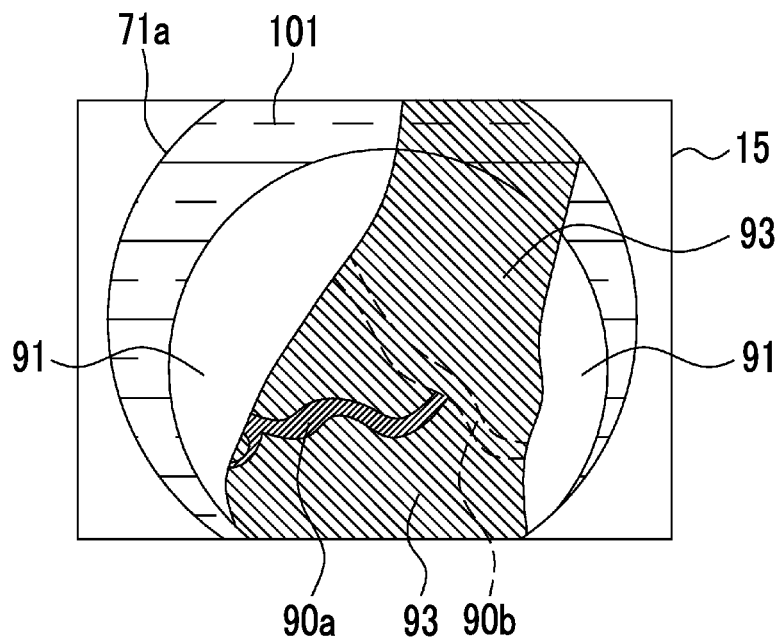
FIG. 10 is an image diagram showing an example of a normal image used for a learning image.

As shown in FIG. 10, specifically, as the learning image, a normal image 71 including a specific blood vessel 90 in an observation target, and a normal image 71a in a case where ESD is performed may be used. The normal image 71a displayed on the display 15 is the normal image 71 in a case where the mucous membrane 91 is incised by locally injecting a local injection solution containing a staining solution such as indigo carmine into the submucosal layer 93 in ESD. In the normal image 71a, a hood 101 attached to the tip of the endoscope, the mucous membrane 91, the submucosal layer 93, a specific blood vessel 90a that is a clearly visible penetrating blood vessel, and a specific blood vessel 90 that is a penetrating blood vessel that is behind the submucosal layer and is not clearly visible are captured. The specific blood vessel 90a that is a clearly visible penetrating blood vessel is the specific blood vessel 90b that normally lurks inside the submucosal layer 93 near the center of the image 71a, that is, on the muscular layer 94 side, and the portion of the specific blood vessel 90b is not visible and indistinguishable from other tissues. In a case where the specific blood vessel 90a and the specific blood vessel 90b are not distinguished, the blood vessels will be referred to as the specific blood vessel 90.

In a case where a doctor associates the information regarding the position of at least a part of the specific blood vessel 90 with the normal image 71a, the positions of the specific blood vessels 90a and 90b are designated on the display 15, and thus, for example, the normal image 71a and coordinates of the specific blood vessels 90a and 90b can be associated.

The information regarding the position of at least a part of the specific blood vessel 90 also includes information that the specific blood vessel 90 is completely absent in a subject captured in the endoscopic image. In a case where there is a blood vessel that is not as thick as the specific blood vessel 90 that is likely to cause problems due to damage but has a thickness that may cause problems, information ranked by thickness such as "thick", "medium", "thin" in the blood vessel may be used. In a case where there is a blood vessel having poor visibility, information ranked with certainty such as "particularly clear", "clear", or "unclear" in the blood vessel may be used. In a case where the specific blood vessel 90 cannot be ascertained before the operation and bleeding occurs during the operation, the information regarding the position of the specific blood vessel 90 obtained from information regarding a bleeding site may be associated with the endoscopic image before the bleeding. A learning image in which the information regarding the position of the specific blood vessel 90 obtained as described above is associated with the endoscopic image is used for learning of the detection unit 83.

Since the detection unit 83 is a learning model having performed learning by using the learning image as described above, in a case where the endoscopic image is input, the detection unit 83 detects the position of the specific blood vessel 90 in the input endoscopic image. The detected position of the specific blood vessel 90 is sent to the information output unit 84.

Figure 11:
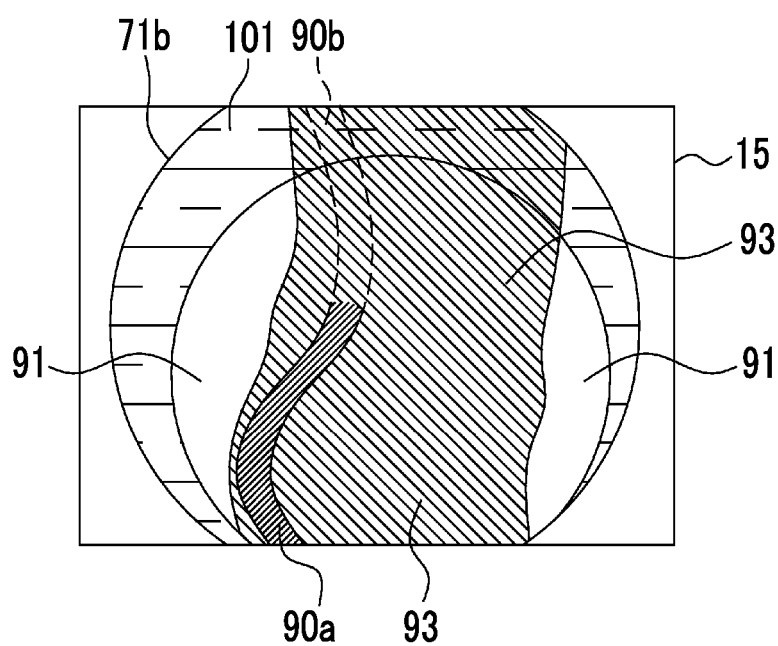
FIG. 11 is an image diagram showing an endoscopic image that is a detection target.

As shown in FIG. 11, the endoscopic image that is a detection target is, for example, the normal image 71b, and the mucous membrane 91, the submucosal layer 93 to which a local injection solution containing a staining solution is locally injected, the specific blood vessel 90b that is a penetrating blood vessel that is behind the submucosal layer and is not clearly visible, and a specific blood vessel 90a that is a clearly visible penetrating blood vessel are captured in the normal image 71b.

The information output unit 84 outputs the position of the specific blood vessel 90 in the endoscopic image, detected by the detection unit 83, as specific blood vessel position information suitable for various outputs. The specific blood vessel position information may be in a format that can be recognized by a person such as a doctor, and examples thereof include a format such as an image, sound, or light. In a case where the specific blood vessel position information is output by an image, the information output unit 84 generates an image indicating the position of the specific blood vessel 90 and uses the imaging as the specific blood vessel position information. The specific blood vessel position information is output to notify a doctor or the like.

Figure 12:
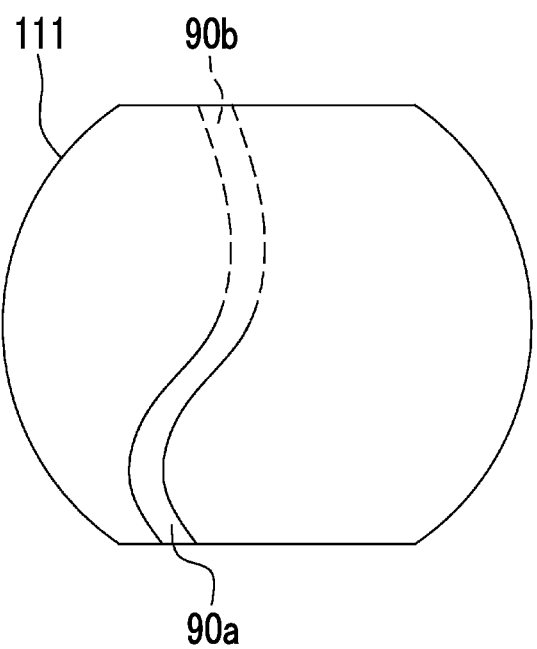
FIG. 12 is an image diagram for describing specific blood vessel position information.

As shown in FIG. 12, specific blood vessel position information 111 that is an image indicating the position of the specific blood vessel 90 is generated to be superimposed on an endoscopic image. In a case where the specific blood vessel position information 111 is adjusted such that the position of the specific blood vessel 90 is displayed on the endoscopic image, the specific blood vessel position information 111 is an image for displaying the specific blood vessels 90a and 90b detected from the endoscopic image on the endoscopic image. The specific blood vessel position information 111 may indicate the specific blood vessel position information 111 regarding the position of the specific blood vessel 90a on the muscular layer 94 side, that is, a position in an outside direction of the lumen wall. For example, the specific blood vessel position information 111 may indicate the specific blood vessel 90a located on the surface side to be emphasized like a solid line, and the specific blood vessel 90b located on the muscular layer 94 side to be more inconspicuous as a dotted line than the specific blood vessel 90a.

For example, in a case where the specific blood vessel position information 111 in the form of an image is displayed on the display 15 in order to provide a notification of the position of the detected specific blood vessel 90, the information display control unit 85 controls display of the specific blood vessel position information 111 such as being aligned with the endoscopic image and then superimposed on the endoscopic image. The endoscopic image on which the specific blood vessel position information 111 is superimposed is generated and displayed on the display 15 by the information display control unit 85.

Figure 13:
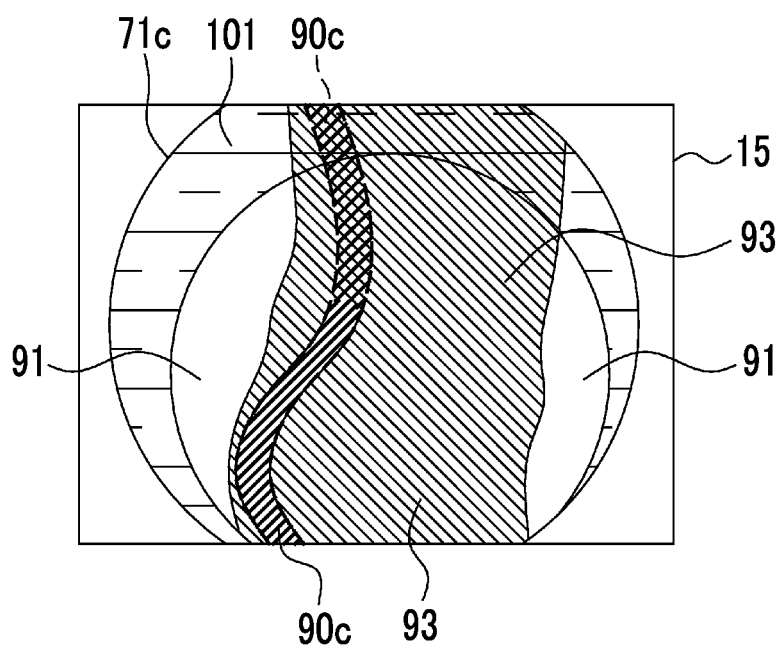
FIG. 13 is an image diagram showing a superimposition image in which the specific blood vessel position information is superimposed on a normal image.

As shown in FIG. 13, in a superimposition image 71c in which the specific blood vessel position information 111 is superimposed on the normal image 71b, which is an endoscopic image generated by the information display control unit 85, the specific blood vessel 90a located near the surface of the submucosal layer 93 and the specific blood vessel 90b located on the muscular layer 94 side of the submucosal layer 93 and having reduced visibility are emphasized with a line of a specific color and are shown as an emphasized specific blood vessel 90c by the specific blood vessel position information 111 on the normal image 71b. The superimposition of the specific blood vessel position information 111 can be turned on and off as appropriate. Therefore, in a case where it is considered that the specific blood vessel position information 111 hinders the progress of ESD, the superimposition of the specific blood vessel position information 111 may be turned off and a normally shown endoscopic image may be used.

As described above, since the medical image processing device 17 detects the position of the specific blood vessel 90 on the basis of the endoscopic image, performing the detection by using the learning image as described above, and performs control for outputting the specific blood vessel position information regarding the position of the specific blood vessel 90 such that a notification thereof is provided, even a blood vessel having reduced visibility in the endoscopic image can be detected and output, for example, as in the superimposition image 71c. Therefore, a doctor can ascertain the position of the specific blood vessel 90b of which the visibility deteriorates from the superimposition image 71c. Specifically, in a case where a doctor performs incision or peeling of the submucosal layer 93 during the ESD operation, the doctor can take measures such as performing hemostasis treatment in advance after ascertaining the position of the specific blood vessel 90b, or performing the incision while avoiding the specific blood vessel 90b. Therefore, during the ESD operation or the like, the doctor can perform incision and peeling of the mucous membrane 91 without damaging the specific blood vessel 90 of which the visibility deteriorates. In a case where a relatively thick blood vessel such as the specific blood vessel 90 is damaged, it takes time and effort to ascertain a bleeding point and to stop bleeding, but it is necessary to improve the efficiency of an operation such as ESD in order not to require the time and effort.

The learning image is preferably an endoscopic image in which an observation target includes the submucosal layer. Since the learning image is an endoscopic image including the submucosal layer 93 (refer to FIG. 11), it is possible to improve the accuracy of detecting the position of the specific blood vessel 90 in the endoscopic image in which the submucosal layer 93 is captured.

The endoscopic image in which the submucosal layer 93 is captured is an endoscopic image in which the mucous membrane 91 is partially incised. The learning image may be an endoscopic image in which an observation target includes a hood or a shadow of the hood. In a case where the mucous membrane 91 is incised, a hood is often attached to the tip of the endoscope. This is because, since the hood has a certain height such as 3 mm or 5 mm from the tip part 12d of the endoscope, a distance from the tip part 12d of the endoscope is constant by bringing the hood into contact with the mucous membrane 91 that is an observation target, and thus the mucous membrane 91 is easily incised or peeled off. Depending on a shape of the hood, the incision or peeling of the submucosal layer 93 may be facilitated by inserting the tip of the hood into the submucosal layer 93. Therefore, by using the endoscopic image (refer to FIG. 11) in which an observation target includes the hood or a shadow of the hood as a learning image, an image during an operation such as ESD can be used as a learning image, and thus it is possible to improve the accuracy of detecting the position of the specific blood vessel 90 in the endoscopic image during an operation such as ESD.

The learning image is preferably an endoscopic image in which an observation target includes fibrosis. In the submucosal layer 93, there may be a tissue called fibrosis in which the connective tissue is abnormally proliferated. Fibrosis is a white fibrous tissue that is thinly formed in the submucosal layer 93 or thickly formed in a case where fibrosis progresses. Since the transparency of the submucosal layer 93 is lost due to the thickness of fibrosis, it may be difficult to visually observe the specific blood vessel 90 or the muscular layer 94 included in the submucosal layer 93. Fibrosis itself may be difficult to distinguish from the muscular layer 94. Fibrosis is a tissue that is harder than the submucosal layer 93, and is thus difficult to incise. Therefore, during the ESD operation, it may be difficult for a doctor to recognize a position of the specific blood vessel 90 indicated in the submucosal layer 93 including fibrosis.

Figure 14:
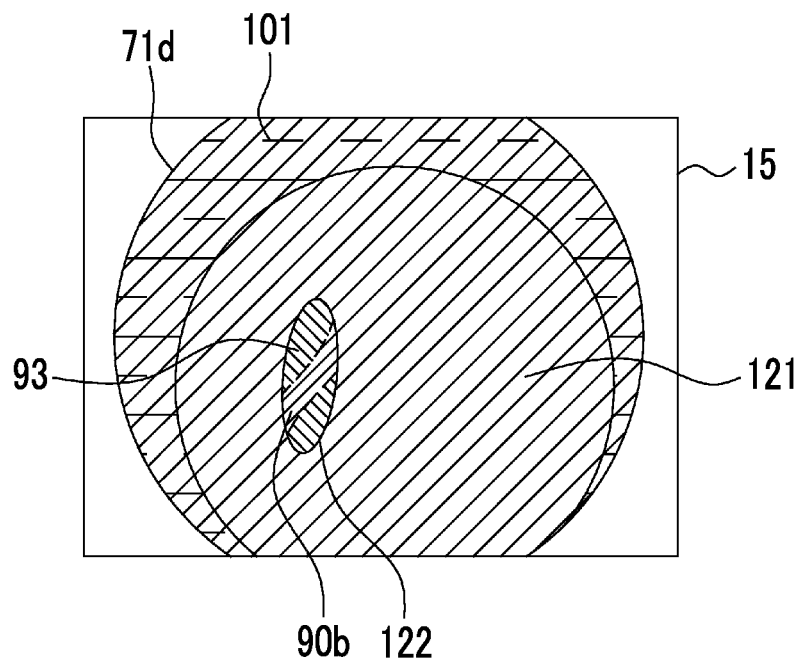
FIG. 14 is an image diagram showing an example of a normal image including fibrosis used for a learning image.

As shown in FIG. 14, the normal image 71d is an endoscopic image including fibrosis 121. The normal image 71d is an endoscopic image during the ESD operation, and in a case where the mucous membrane 91 is incised, the fibrosis 121 is spread, and a thin fibrosis region 122 is present in a part of the fibrosis 121. In the thin fibrosis region 122, the submucosal layer 93 in which a blue local injection solution is seen through and the specific blood vessel 90b indicated in the submucosal layer 93 are partially visible. Therefore, in a case where the normal image 71d is used as a learning image, information regarding a position of the specific blood vessel 90d partially visible in the normal image 71d is used in association with the normal image 71d.

Since the learning image is an endoscopic image including fibrosis, it is possible to improve the accuracy of detecting a position of the specific blood vessel 90 in the endoscopic image in which the fibrosis is captured.

The learning image is preferably an endoscopic image in which an observation target includes cautery scars, coagulated blood, and/or fat. The inner wall of the digestive tract that is a target of ESD may include cautery scars for hemostasis in EMR or ESD performed previously, coagulated blood in which bleeding is coagulated, fat, and the like. Therefore, it is necessary to accurately detect the specific blood vessel 90 from these tissues and the like.

Figure 15:
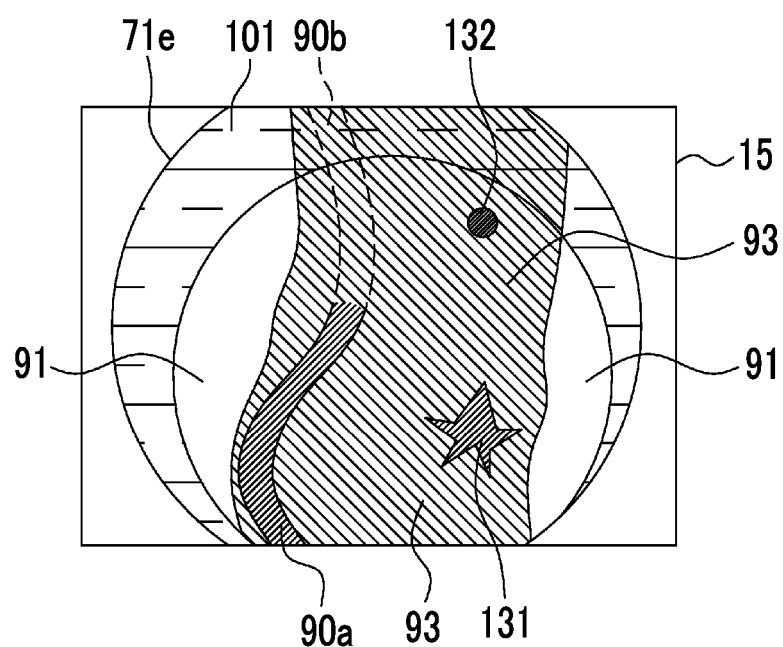
FIG. 15 is an image diagram showing an example of a normal image including a cautery scar and coagulated blood used for a learning image.

As shown in FIG. 15, a normal image 71e is an endoscopic image including a cautery scar 131 and coagulated blood 132. By using the endoscopic image 71e as a learning image, the specific blood vessel 90 can be detected accurately from these tissues and the like.

The learning image is preferably an endoscopic image associated with information obtained by performing image processing on the endoscopic image. The learning image is preferably an endoscopic image obtained by imaging an observation target illuminated by illumination light having a predetermined spectrum.

Examples of the image processing include image processing of emphasizing a specific structure captured in the endoscopic image, and image processing of enhancing a color tone in the vicinity of a mucous membrane color. The specific structure includes a blood vessel. The inner wall of the digestive tract may be used as a surface, and among blood vessels, image processing may be performed to emphasize superficial blood vessels present in a surface layer, middle blood vessels in a middle layer, or deep blood vessels in a deep layer.

Examples of a method of emphasizing superficial blood vessels, middle blood vessels, or deep blood vessels includes a method of obtaining information regarding a blood vessel having a specific depth by using a brightness ratio of each obtained image with respect to a plurality of endoscopic images obtained through imaging by using a plurality of types of specific narrow-band light as illumination light, and a method of obtaining information by imaging an observation target illuminated by illumination light having a predetermined spectrum.

Figure 16:
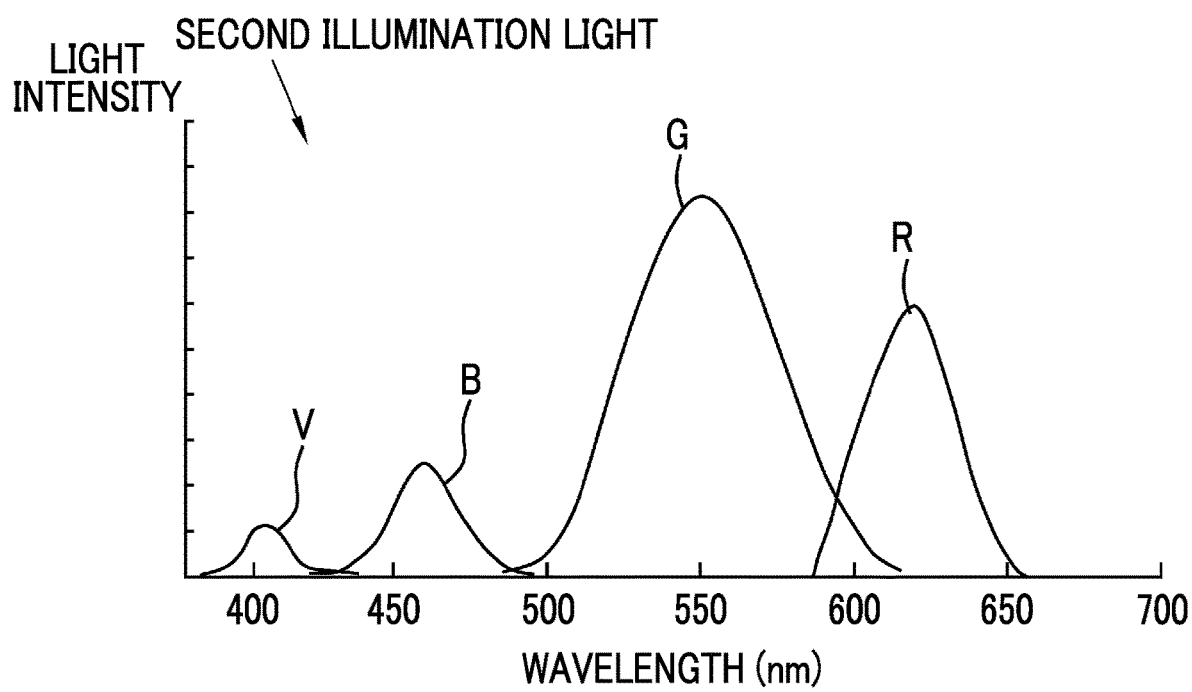
FIG. 16 is a graph showing a spectrum of second illumination light.

For example, examples of the illumination light having a predetermined spectrum include the first illumination light (refer to FIG. 5) and the second illumination light (refer to FIG. 16). In a case where the special observation mode is set, the light source processor 21 may control the respective LEDs 20a to 20d such that the second illumination light in which a combination of the light intensity ratios between the violet light V, the blue light B, the green light G, and the red light R is Vs2:Bs2:Gs2:Rs2 is emitted. The second illumination light is preferably used to emphasize deep blood vessels. Thus, in the second illumination light, it is preferable that the light intensity of the blue light B is higher than the light intensity of the violet light V. For example, as shown in FIG. 16, a ratio between the light intensity Vs2 of the violet light V and the light intensity Bs2 of the blue light B is set to "1:3".

Figure 17:
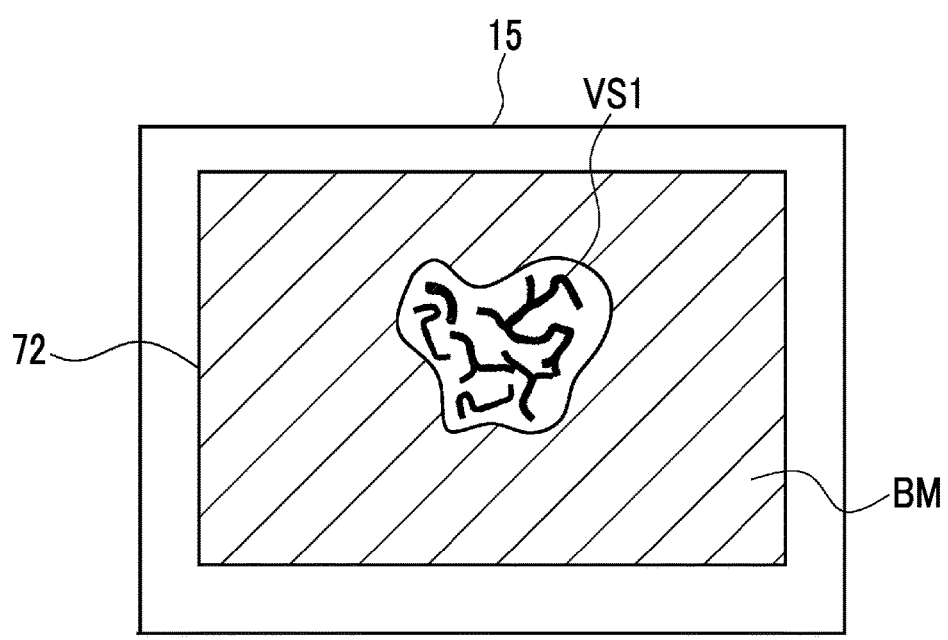
FIG. 17 is an image diagram showing a first image.
Figure 18:
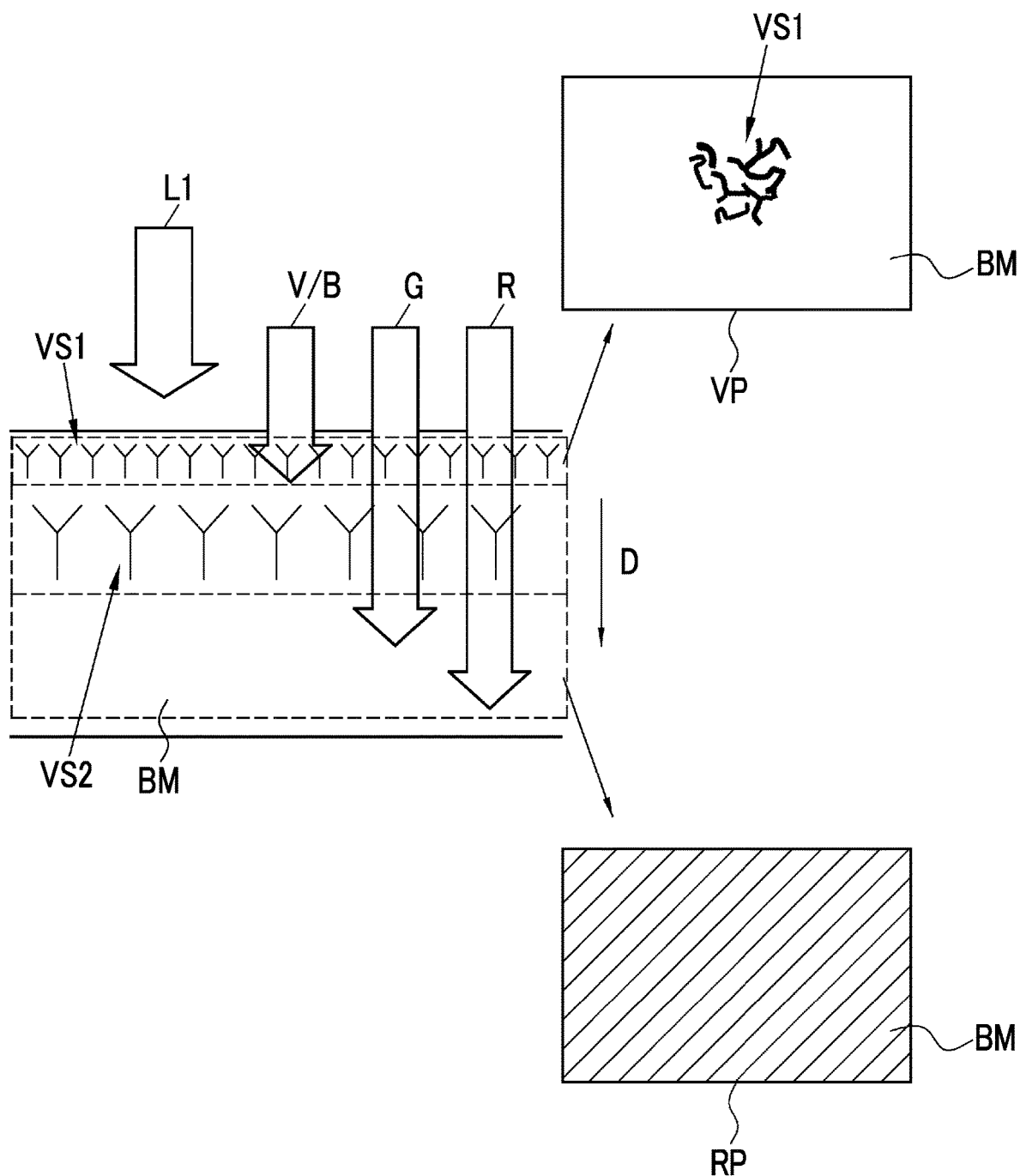
FIG. 18 is an explanatory diagram showing a violet and blue light image and a green and red light image obtained in a case where illumination of the first illumination light is provided.

As described above, according to the first image 72 obtained by using the first illumination light, as shown in FIG. 17, an image showing background mucous membrane BM and a superficial blood vessel VS1 among observation targets is displayed. The first image 72 is obtained on the basis of the first illumination light including violet light, blue light, green light, and red light. As shown in FIG. 18, in a case where the first illumination light L1 illuminates the observation target, the violet light and the blue light V/B of the first illumination light L1 reach the surface layer where the superficial blood vessels VS1 are distributed. In FIG. 18, the first illumination light L1 illuminates the observation target from above the paper surface, and the lower side of the paper surface is a depth direction D of the observation target. Since the light intensity of the violet light V is higher than the light intensities of the blue light B, the green light G, and the red light R in the first illumination light, an image of the superficial blood vessels VS1 included in a violet light image VP obtained on the basis of reflected light of the violet light V is emphasized. Here, since the light intensity of the violet light V is higher than the light intensities of the blue light B, the green light G, and the red light R, the violet light image VP is used. The red light R of the first illumination light L1 reaches the background mucous membrane BM distributed at a position deeper than the superficial blood vessel VS1 and the deep blood vessel VS2 (a blood vessel located at a position deeper than the superficial blood vessel VS1). Therefore, a red light image RP obtained on the basis of reflected light of the red light R includes an image of the background mucous membrane BM. From the above description, since the first image is an image in which the violet light image VP and the red light image RP are combined, the images of the background mucous membrane BM and the superficial blood vessel VS1 are displayed.

Figure 19:
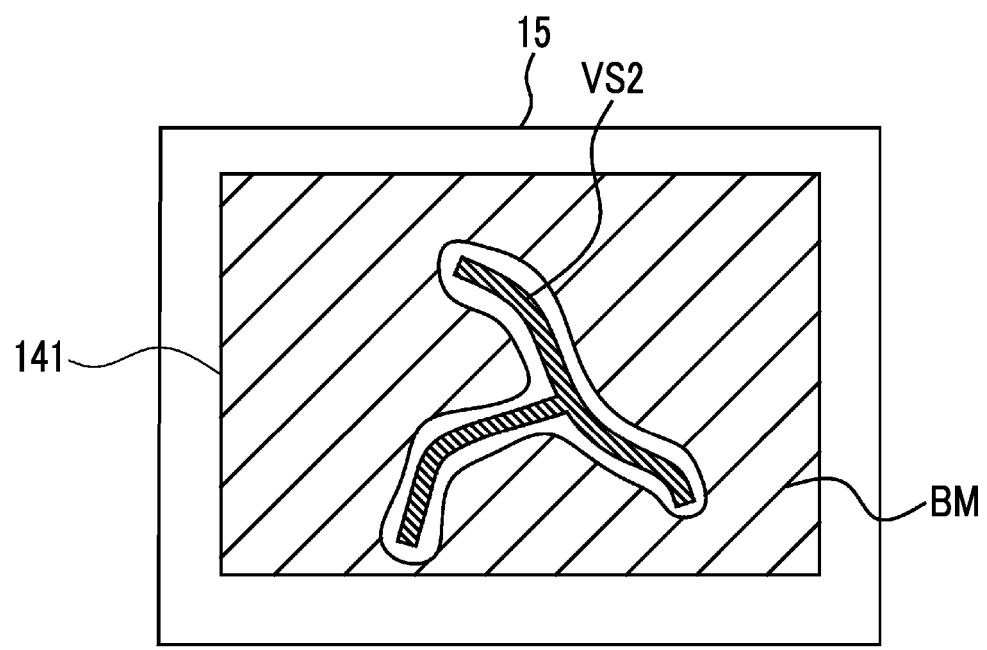
FIG. 19 is an image diagram showing a second image.
Figure 20:
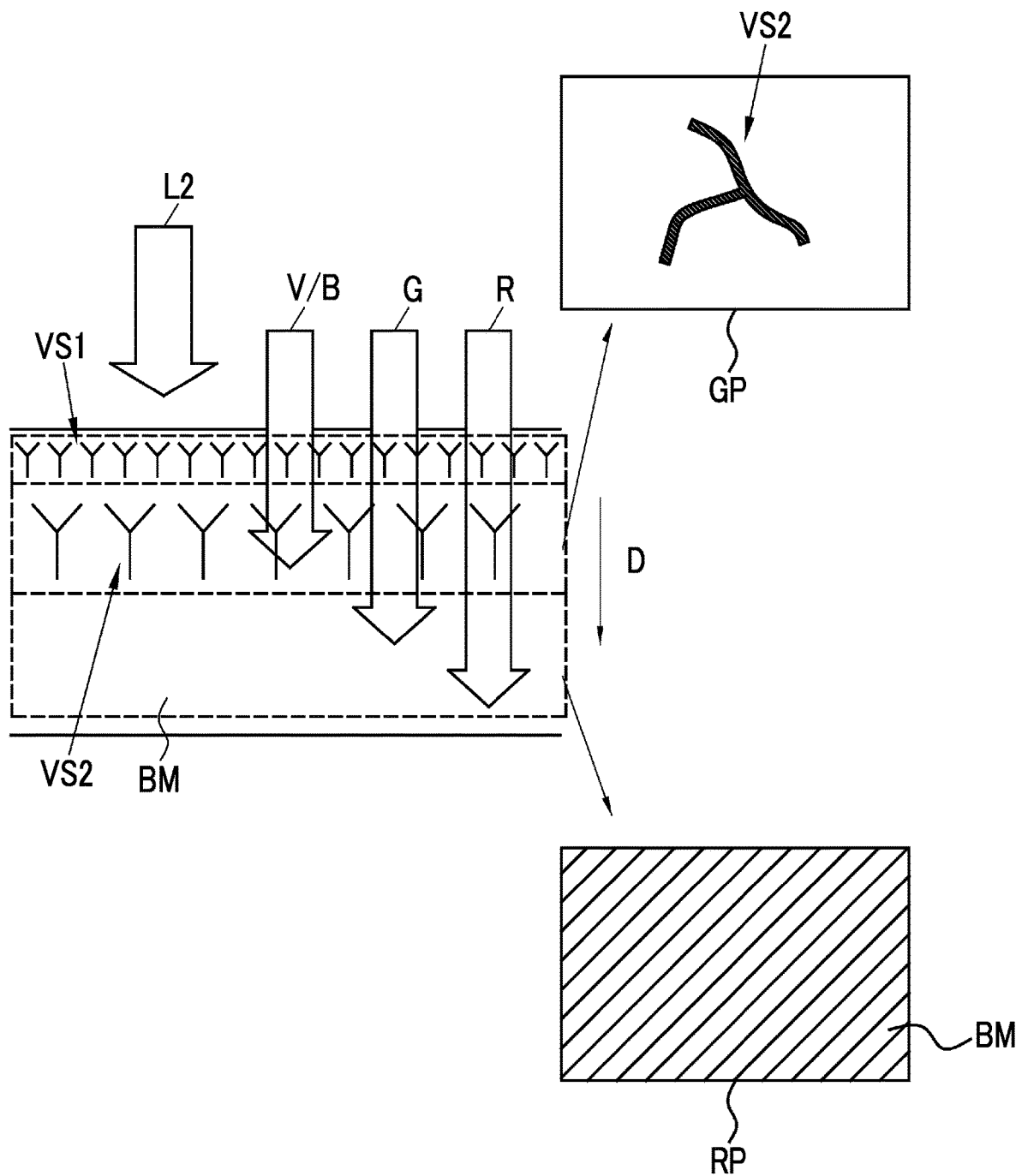
FIG. 20 is an explanatory diagram showing a violet and blue light image and a green and red light image obtained in a case where illumination of the second illumination light is provided.

As shown in FIG. 19, a second image 141 obtained by using the second illumination light displays an image showing the background mucous membrane BM and the deep blood vessel VS2 among the observation objects. The second image 141 is obtained on the basis of the second illumination light including the violet light V, the blue light B, the green light G, and the red light R. As shown in FIG. 20, the green light G of the second illumination light L2 reaches the deep layer where the deep blood vessels VS2 are distributed. In FIG. 20, the second illumination light L2 illuminates the observation target from above the paper surface, and the lower side of the paper surface is the depth direction D of the observation target. In the second illumination light L2, since the light intensity of the green light G is higher than the light intensities of the blue light B, the violet light V, and the red light R, an image of the deep blood vessel VS2 included in the green light image GP obtained on the basis of reflected light of the green light G is emphasized. Here, since the light intensity of the green light G is high, the green light image GP is used. The red light R of the second illumination light L2 reaches the background mucous membrane BM distributed at a position deeper than the superficial blood vessel VS1 and the deep blood vessel VS2 (a blood vessel located at a position deeper than the superficial blood vessel VS1). Therefore, a red light image RP obtained on the basis of reflected light of the red light R includes an image of the background mucous membrane BM. From the above description, since the second image is an image in which the green light image GP and the red light image RP are combined, the images of the background mucous membrane BM and the deep blood vessel VS2 are displayed.

As described above, the first image 72 is an endoscopic image in which the superficial blood vessel VS1 is emphasized, and the second image 141 is an endoscopic image in which the deep blood vessel VS2 is emphasized. These endoscopic images may be used as learning images. Since the learning image is an endoscopic image in which blood vessels are emphasized, it is possible to improve the accuracy of detecting the position of the specific blood vessel 90 in the endoscopic image.

Since the learning image is an endoscopic image associated with information obtained by performing image processing on the endoscopic image, the information can be associated with the endoscopic image more broadly or accurately. Specifically, in a case where the specific blood vessel 90 is included in the deep blood vessel emphasized and displayed by performing image processing on the endoscopic image, information regarding the specific blood vessel 90 can be associated with the endoscopic image. Therefore, by using such an endoscopic image as a learning image, a wider range of information or more detailed information can be associated with the learning image, and thus the detection unit 83 is likely to detect the specific blood vessel 90 more accurately.

As described above, the normal light, and the first illumination light or the second illumination light can be automatically switched in the multi-observation mode. It can be said that, among these types of illumination light, the endoscopic image obtained by illuminating the normal light is displayed on the display 15, and the endoscopic image obtained by illuminating special light such as the first illumination light and the second illumination light is not displayed on the display 15. The endoscopic image obtained by illuminating special light may be used for performing image processing to obtain various types of information, and may be stored to be used as a learning image.

It is preferable that the specific blood vessel position information includes information regarding an incision suitable site where safe incision is possible. The incision suitable site is a site where at least the specific blood vessel 90 is unlikely to be damaged in a case where the mucous membrane or the like is incised in ESD or the like.

Figure 21:
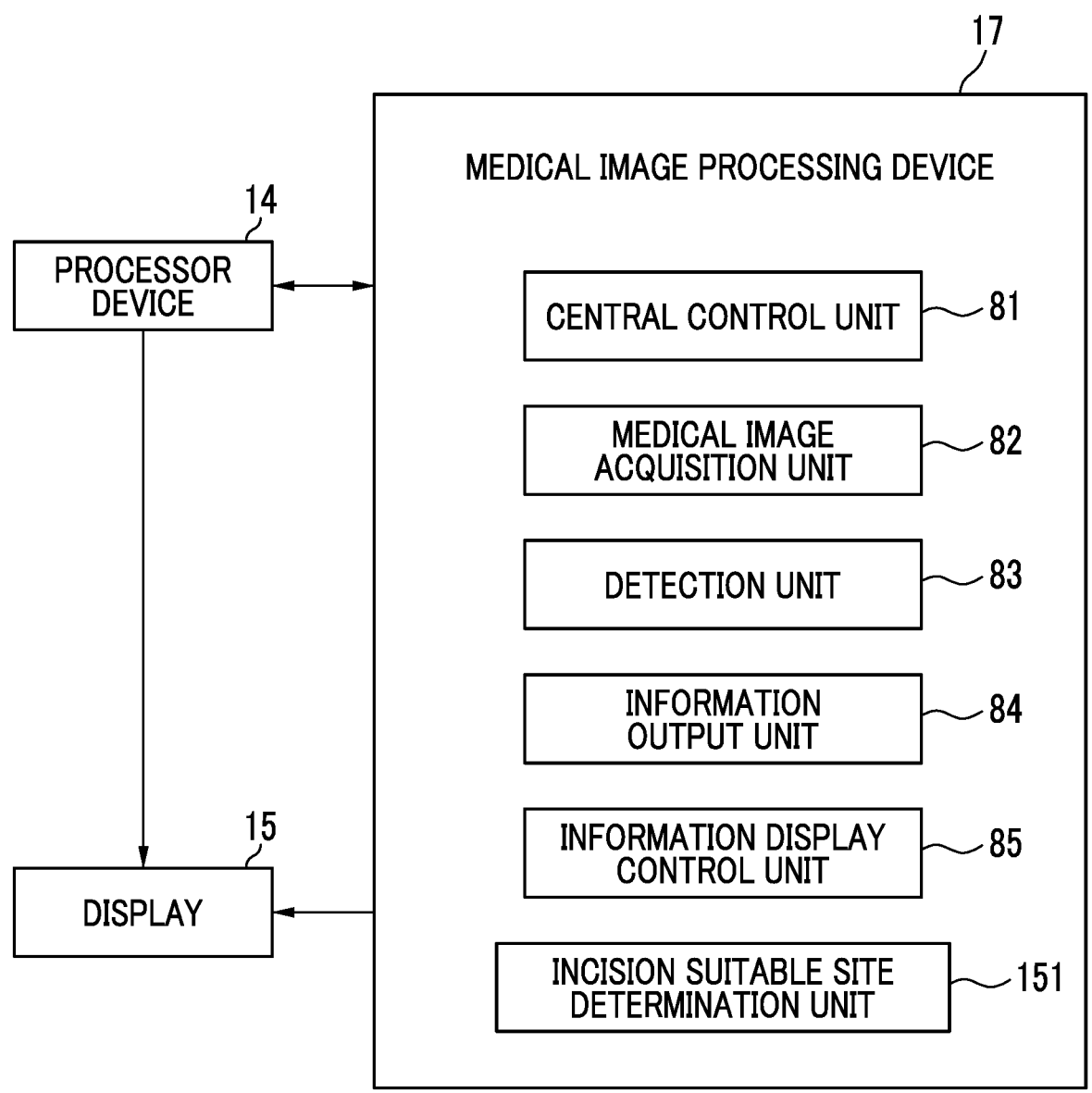
FIG. 21 is a block diagram showing a function of a medical image processing device in which a reference information acquisition unit includes an incision suitable site determination unit.

As shown in FIG. 21, the medical image processing device 17 includes an incision suitable site determination unit 151. On the basis of a position of the specific blood vessel 90 detected by the detection unit 83, the incision suitable site determination unit 151 determines a region that is unlikely to damage the specific blood vessel 90 even though incision is performed in the observation target captured in the endoscopic image, and generates information regarding an incision suitable site. It can be said that the farther the region is from the specific blood vessel 90, the less likely it is that the specific blood vessel 90 will be damaged even though the incision is made. A distance from the specific blood vessel 90 may be a two-dimensional distance in the endoscopic image or a three-dimensional distance from the mucous membrane 91 toward the muscular layer 94. The information regarding the incision suitable site may be superimposed and displayed on the endoscopic image as, for example, a figure shape in order to notify a doctor.

Figure 22:
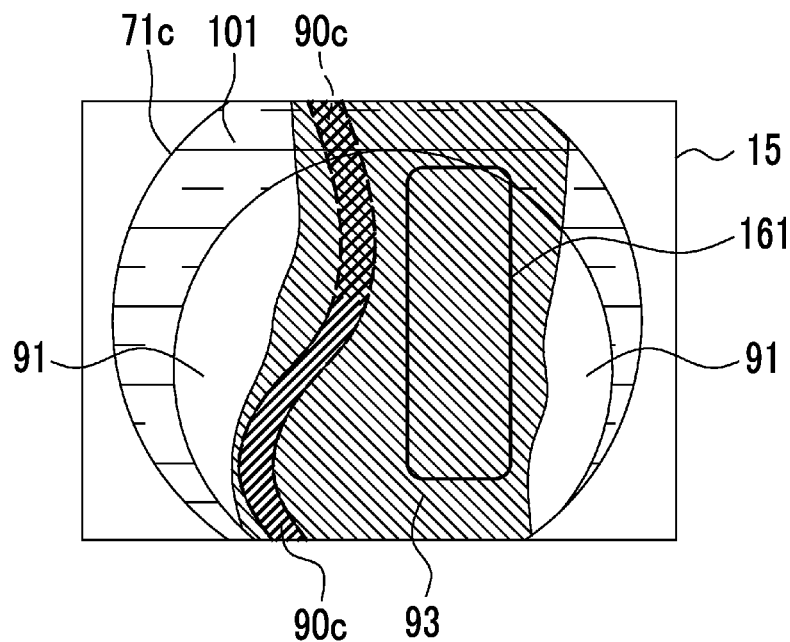
FIG. 22 is an image diagram of a superimposition image displaying an example of an incision suitable site indication.

As shown in FIG. 22, an incision suitable site indication 161 is displayed by superimposing the information regarding the incision suitable site on the normal image 71c as a figure shape. By viewing the incision suitable site indication 161, the doctor can recognize that a probability of damaging the specific blood vessel 90 is low in a case where making an incision within a range of the incision suitable site indication 161. It is preferable that the emphasized specific blood vessel 90c is also displayed on the normal image 71c.

The endoscopic image displaying the incision suitable site indication 161 and the emphasized specific blood vessel 90c allows the doctor to perform ESD while ascertaining the position of the specific blood vessel 90 and the incision suitable site at a glance.

It is preferable that the medical image processing device 17 performs control for outputting the specific blood vessel position information with at least one of a color, a figure, a symbol, and a character. It is preferable that the medical image processing device 17 performs control for outputting the specific blood vessel position information with sound and/or light.

Figure 23:
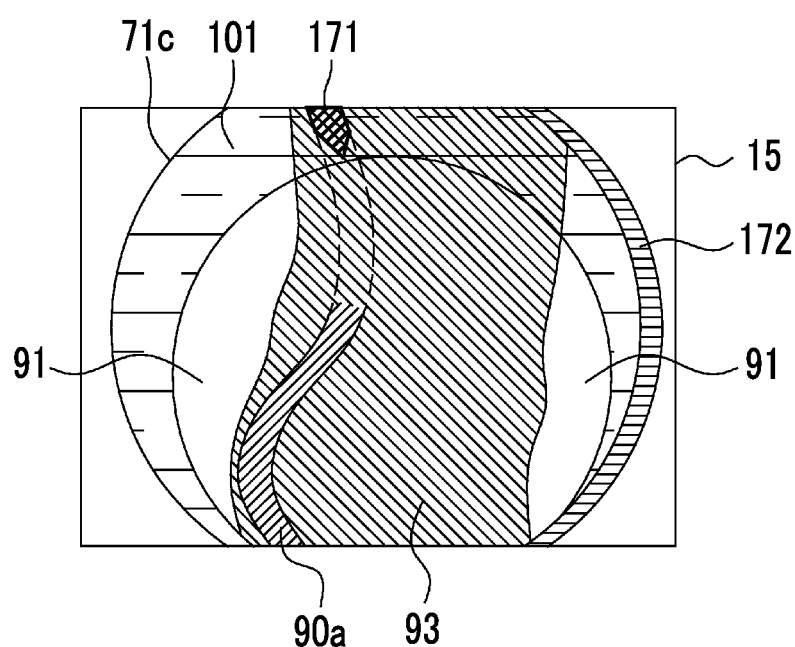
FIG. 23 is an image diagram of a superimposition image displaying another example of an incision suitable site indication.

The specific blood vessel position information is indicated by a line of a specific color (refer to FIG. 13), and may also be displayed by combining figures, symbols, and/or characters. As shown in FIG. 23, for example, in a case where the specific blood vessel position information is shown on the endoscopic image, the specific blood vessel position information 171 indicates the presence and the direction the specific blood vessel 90b that is not clearly visible behind the submucosal layer at the end of the endoscopic image.

Similarly, the incision suitable site indication is also controlled to be output with at least one of a color, a figure, a symbol, and a character. As shown in FIG. 23, for example, an incision suitable site indication 172 is displayed to indicate a direction in which the incision suitable site is present in a color suggesting safety, such as blue, outside the frame on the side of the endoscopic image where the specific blood vessel 90 is not present. In a case where the specific blood vessel 90 is present, the incision suitable site indication 172 may display a direction in which the incision suitable site is not present in a color suggesting a danger, such as yellow, outside the frame on the side of the endoscopic image where the specific blood vessel 90 is present.

In a case where the specific blood vessel position information is output with sound and/or light, for example, a position of a treatment tool such as a knife in the endoscopic image is determined, and in a case where the treatment tool approaches the specific blood vessel 90, a doctor or the like may be notified of the position of the treatment tool with sound and/or light. In the case of providing the notification with sound, sound may be emitted in a case where the treatment tool approaches the specific blood vessel 90, and the sound may become louder as the treatment tool approaches the specific blood vessel 90. Similarly, in the case of providing the notification with light, in a case where the treatment tool approaches the specific blood vessel 90, a lamp installed in a casing of the medical image processing device 17 or the like or light in the display 15 or an endoscopic image displayed on the display 15 may be blinked, and a blinking interval may become shorter as the treatment tool approaches the specific blood vessel 90.

By outputting the specific blood vessel position information with at least one of a color, a figure, a symbol, or a character, or with sound and/or light, for example, it is possible to accurately and effectively indicate a position of a specific blood vessel to a doctor so as not to interfere with the progress of ESD.

Figure 24:
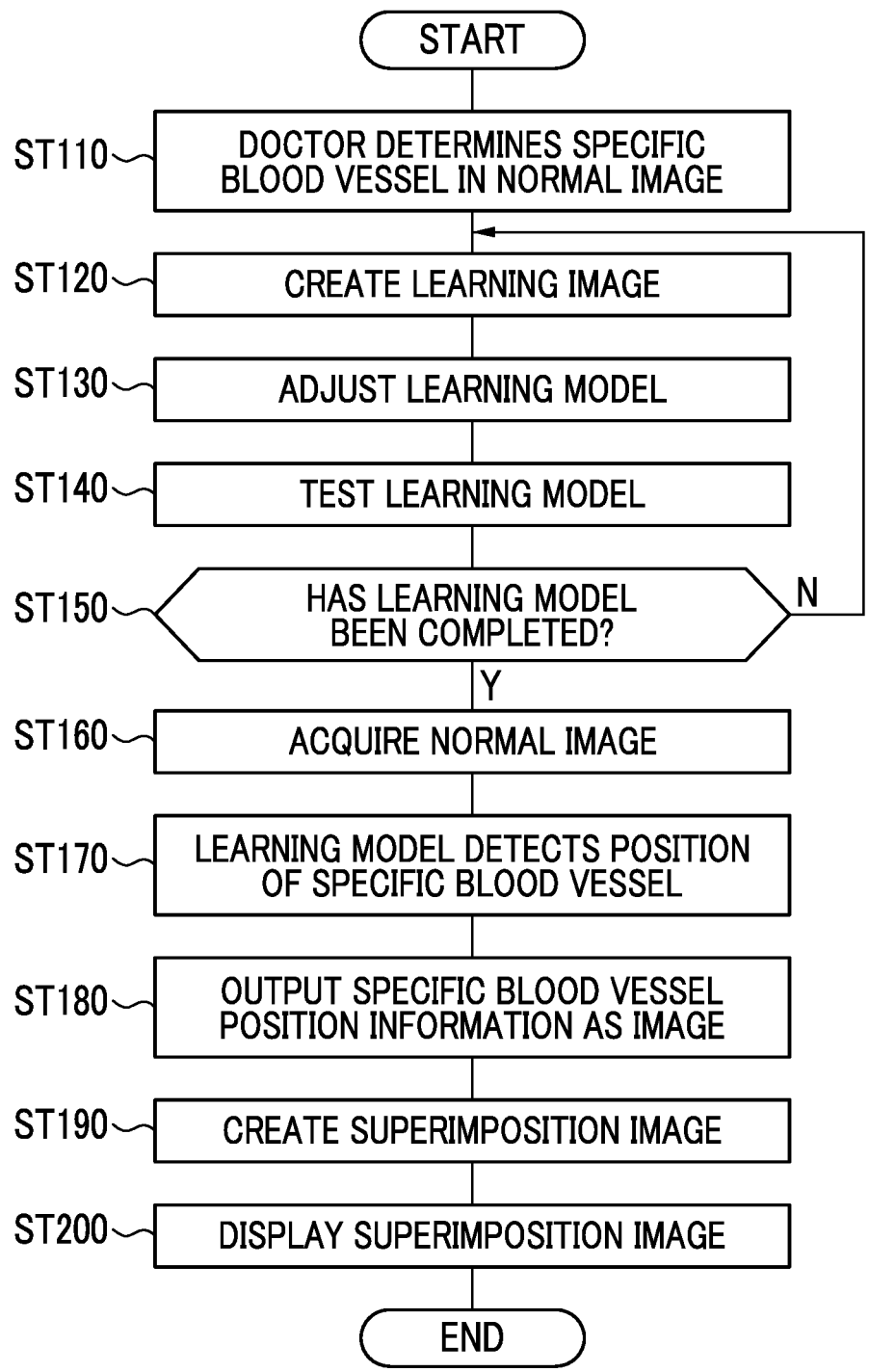
FIG. 24 is a flowchart for describing a flow of a series of processes of the medical image processing device.

A flow of a series of endoscopic image processes of the present embodiment by the medical image processing device 17 will be described with reference to a flowchart of FIG. 24. First, in order to create a learning image, a doctor determines a position of the specific blood vessel 90 in a subject captured in a normal image (step ST110). Next, a learning image in which the position of the specific blood vessel 90 is associated with the normal image is created (step ST120). A learning model having learned the learning image is created by using the learning image, and is adjusted such that a position of the specific blood vessel is correctly detected by using an endoscopic image of a test case or the like (step ST130). The learning model is tested by using an endoscopic image from which a position of the specific blood vessel is desired to be detected (step ST140). In a case where the learning model detects a position of the specific blood vessel as desired, the learning model is completed (Y in step ST150). In a case where there is a problem in detecting a position of the specific blood vessel in the learning model, the process returns to the creation of the learning image and the learning model is recreated (N in step ST150). In a case where the learning model is completed, a normal image from which a position of the specific blood vessel is desired to be detected is acquired (step ST160). The learning model detects a position of the specific blood vessel on the basis of a normal image (step ST170). Specific blood vessel position information displaying the detected position of the specific blood vessel is output as an image (step ST180). An image of the specific blood vessel position information is superimposed on the normal image (step ST190). The superimposition image is displayed on the display 15 (step ST200).

In the above embodiment, the present invention is applied to the case of processing an endoscopic image, but is also applicable to a processor device a medical image processing device, a medical image processing system, or the like processing a medical image other than an endoscopic image.

Figure 25:
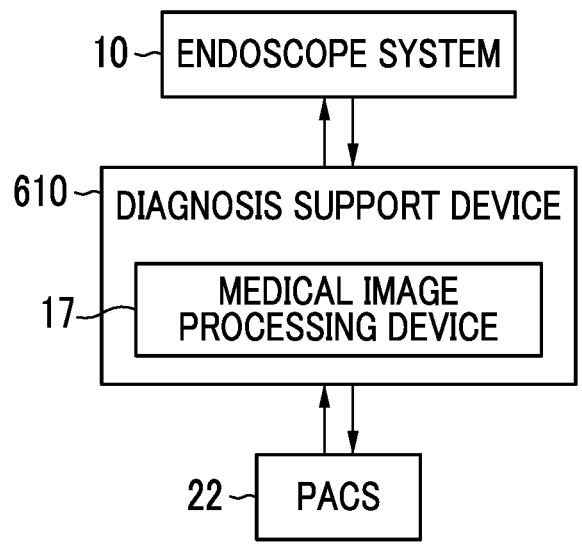
FIG. 25 is an explanatory diagram for describing a case where a medical image processing device is included in a diagnosis support device.

As shown in FIG. 25, a part or the whole of the image processing unit 55 and/or the central control unit 58 of the endoscope system 10 may be provided in a diagnosis support device 610 that acquires an image picked up by the endoscope 12 directly from the endoscope system 10 or indirectly from a picture archiving and communication systems (PACS) 22. Similarly, a part or the whole of the medical image processing device 17 of the endoscope system 10 may be provided in a diagnosis support device 610 that acquires an image picked up by the endoscope 12 directly from the endoscope system 10 or indirectly from a picture archiving and communication systems (PACS) 22.

Figure 26:
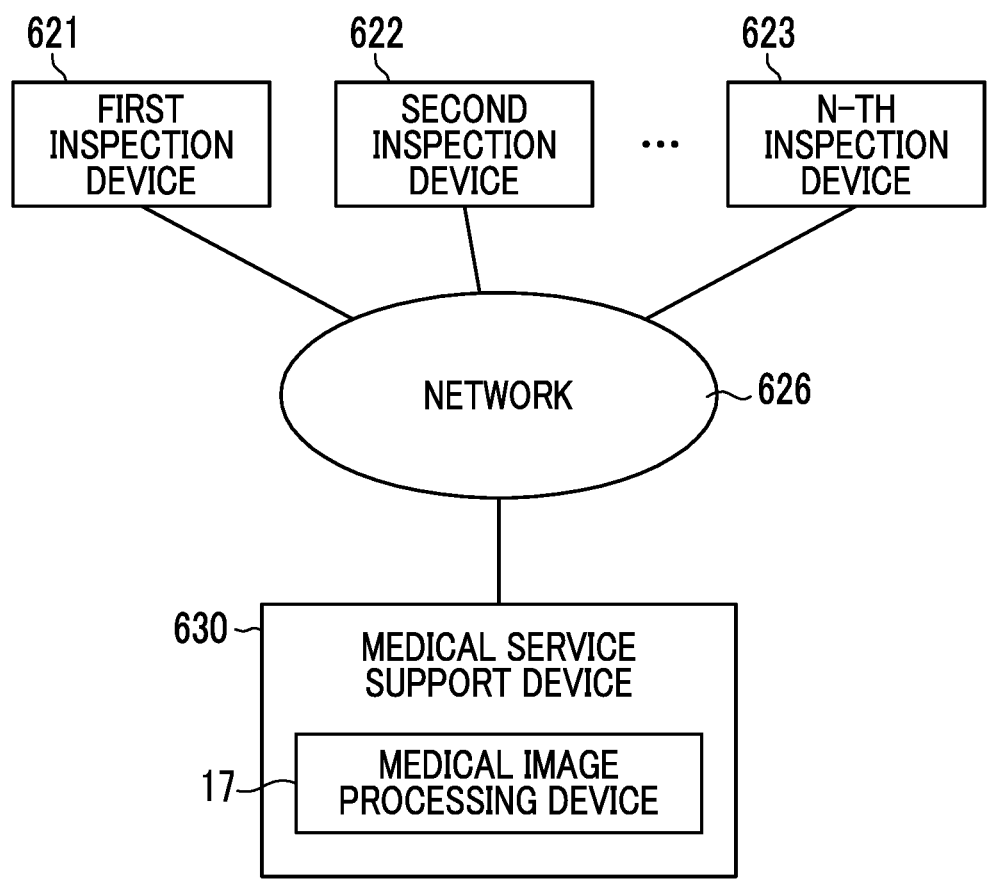
FIG. 26 is an explanatory diagram for describing a case where a medical image processing device is included in a medical service support device.

As shown in FIG. 26, a part or the whole of the image processing unit 55 and/or the central control unit 58 or a part or the whole of the medical image processing device 17 of the endoscope system 10 may be provided in a medical service support device 630 including the endoscope system 10 and connected to various examination devices such as a first examination device 621, a second examination device 622, . . . , and an N-th examination device 623 via a network 626.

In the above embodiment, hardware structures of processing units executing various processes, such as the light source processor, the central control unit 58, the image acquisition unit 51, the DSP 52, the noise reduction unit 53, the memory 54, the image processing unit 55, the display control unit 56, and the video signal generation unit 57 which are included in the processor device 14 including the first processor, and the central processing unit 81, the medical image acquisition unit 82, the detection unit 83, the information output unit 84, the information display control unit 85, and the incision suitable site determination unit 151 that are included in the medical image processing device 17 including the second processor are various processors as described below. The various processors include a programmable logic device (PLD), which is a processor of which a circuit configuration can be changed after manufacturing, such as a central processing unit (CPU) or a field programmable gate array (FPGA) that is a general-purpose processor that executes software (programs) and functions as various processing units, a dedicated electric circuit that is a processor having a circuit configuration specially designed to execute various processes, and the like.

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined.

EXPLANATION OF REFERENCES 10 endoscope system
12: endoscope
12a: insertion part
12b: operating part
12c: bendable part
12d: tip part
12e: angle knob
12f: zoom operating part
12g: mode selector switch
12h: forceps port
13: light source device
14: processor device
15: display
16: keyboard
17: medical image processing device
20: light source unit
20a: V-LED
20b: B-LED
20c: G-LED
20d: R-LED
21: light source processor
22: PACS
30a: Illumination optical system
30b: image pick-up optical system
41: light guide
42: illumination lens
43: objective lens
44: zoom lens
45: image pick-up sensor
46: CDS/AGC circuit
47: A/D converter
51: image acquisition unit
52: DSP
53: noise reduction unit
54: memory
55: image processing unit
56: display control unit
57: video signal generation unit
58, 81: central control unit
61: normal image processing unit
62: special image processing unit
71, 71a, 71b, 71c, 71d: normal image
72: first image
82: medical image acquisition unit
83: detection unit
84: information output unit
85: information display control unit
90, 90a, 90b: specific blood vessel
90c: emphasized specific blood vessel
91: mucous membrane
92: muscularis mucosae
93: submucosal layer
94: muscular layer
95: serosa
96: penetrating blood vessel
97: vein
98: lymphatic vessel
99: arteries
101: hood
111, 171: specific blood vessel position information
121: fibrosis
122: region of thin fibrosis
131: cautery scar
132: coagulated blood
141: second image
151: incision suitable site determination unit
161, 172: incision suitable site indication
610: diagnosis support device
621: first examination device
622: second examination device
623: N-th examination device
626: network
630: medical service support device
VS1: superficial blood vessel
VS2: deep blood vessel
BM: background mucous membrane
L1: first illumination light
L2: second illumination light
V/B: violet light and blue light
G: green light
R: red light
D: depth direction
VP: violet light image
BP: blue light image
RP: red light image
X: inside direction of large intestine
D: depth direction
ST110 to ST200: step

What is claimed is:

1. A medical image processing device comprising:
a processor configured to:
acquire a medical image obtained by imaging a subject with an endoscope;
detect a position of a specific blood vessel that is a blood vessel included in the subject captured in the medical image and has a predetermined thickness or more on the basis of the medical image; and
perform control for outputting specific blood vessel position information regarding the position of the specific blood vessel to provide a notification, and
wherein
the detection of the position of the specific blood vessel is performed by using a learning image that is the medical image associated with information regarding a position of at least a part of the specific blood vessel included in the subject captured in the medical image, the processor is configured to include a learning model that has performed learning by using the learning image to detect a position of a specific blood vessel in an observation target by inputting an image that captures the observation target, and the detection of the specific blood vessel is performed by using the learning model.

2. The medical image processing device according to claim 1, wherein
the learning image is the medical image in which the subject includes a submucosal layer.

3. The medical image processing device according to claim 1, wherein
the learning image is the medical image in which the subject includes fibrosis.

4. The medical image processing device according to claim 1, wherein
the learning image is the medical image in which the subject includes a cautery scar, coagulated blood, and/or fat.

5. The medical image processing device according to claim 1, wherein
the learning image is the medical image associated with information indicating that there is no specific blood vessel.

6. The medical image processing device according to claim 1, wherein
the learning image is the medical image associated with information obtained by a doctor visually observing the medical image.

7. The medical image processing device according to claim 1, wherein
the learning image is the medical image associated with information obtained by performing image processing on the medical image.

8. The medical image processing device according to claim 1, wherein
the learning image is the medical image associated with information obtained by performing image processing on the medical image obtained by imaging the subject illuminated by illumination light having a predetermined spectrum.

9. The medical image processing device according to claim 1, wherein
the specific blood vessel position information includes information regarding an incision suitable site where safe incision is possible.

10. The medical image processing device according to claim 1, wherein
the processor is configured to perform control for outputting the specific blood vessel position information with at least one of a color, a figure, a symbol, and a character.

11. The medical image processing device according to claim 1, wherein
the processor is configured to perform control for outputting the specific blood vessel position information with sound and/or light.

12. An endoscope system comprising:
the medical image processing device according to claim 1;
a light source that emits illumination light that illuminates a subject; and
an endoscope that images the subject.

13. The medical image processing device according to claim 1, wherein
the specific blood vessel having reduced visibility is emphasized and shown as an emphasized specific blood vessel.

14. A medical image processing device operation method comprising:
acquiring a medical image obtained by imaging a subject with an endoscope;
detecting a position of a specific blood vessel that is a blood vessel included in the subject captured in the medical image and has a predetermined thickness or more on the basis of the medical image; and
performing control for outputting specific blood vessel position information regarding the position of the specific blood vessel to provide a notification, wherein
the detection of the position of the specific blood vessel is performed by using a learning image that is the medical image associated with information regarding a position of at least a part of the position of the specific blood vessel included in the subject captured in the medical image,
the method uses a learning model that has performed learning by using the learning image to detect a position of a specific blood vessel in an observation target by inputting an image that captures the observation target, and
the detection of the specific blood vessel is performed by using the learning model.

* * * * *